US011719695B2

(12) United States Patent
Takeuchi et al.

(10) Patent No.: US 11,719,695 B2
(45) Date of Patent: Aug. 8, 2023

(54) IMMUNOASSAY METHOD TO PREVENT INHIBITION OF ANTIGEN-ANTIBODY BINDING INTERACTIONS IN MUCOSAL FLUIDS

(71) Applicants: NH Foods Ltd., Osaka (JP); National Agriculture and Foods Research Organization, Tsukuba (JP)

(72) Inventors: Eri Takeuchi, Tsukuba (JP); Kana Urayama, Tsukuba (JP); Takashi Matsumoto, Tsukuba (JP); Kazuki Morioka, Tsukuba (JP); Makoto Yamakawa, Tsukuba (JP); Kazuo Yoshida, Tsukuba (JP); Toru Kanno, Tsukuba (JP); Katsuhiko Fukai, Tsukuba (JP)

(73) Assignees: NH Foods Ltd, Osaka (JP); National Agriculture and Food Research Organization, Ibaraki (JP)

( * ) Notice: Subject to any disclaimer, the term of this patent is extended or adjusted under 35 U.S.C. 154(b) by 746 days.

(21) Appl. No.: 16/498,579

(22) PCT Filed: Mar. 27, 2018

(86) PCT No.: PCT/JP2018/012330
§ 371 (c)(1),
(2) Date: Dec. 10, 2019

(87) PCT Pub. No.: WO2018/181263
PCT Pub. Date: Oct. 4, 2018

(65) Prior Publication Data
US 2020/0166436 A1 May 28, 2020

(30) Foreign Application Priority Data
Mar. 27, 2017 (JP) ................................. 2017-061335

(51) Int. Cl.
*G01N 33/569* (2006.01)
*G01N 1/28* (2006.01)
(52) U.S. Cl.
CPC ..... *G01N 33/569* (2013.01); *G01N 33/56911* (2013.01); *G01N 33/56983* (2013.01); *G01N 1/28* (2013.01); *G01N 2800/26* (2013.01)
(58) Field of Classification Search
CPC ........... G01N 33/569; G01N 33/56911; G01N 33/56983
See application file for complete search history.

(56) References Cited

U.S. PATENT DOCUMENTS

| 8,524,452 B2* | 9/2013 | Minakawa | G01N 33/52 435/7.1 |
|---|---|---|---|
| 2003/0203423 A1 | 10/2003 | Okada et al. | |
| 2005/0118595 A1 | 6/2005 | Lahann | |
| 2008/0166701 A1 | 7/2008 | Ohmiya et al. | |
| 2010/0143933 A1 | 6/2010 | Minakawa et al. | |
| 2011/0053181 A1 | 3/2011 | Hazama et al. | |
| 2012/0107953 A1 | 5/2012 | Schneider | |
| 2013/0029429 A1 | 1/2013 | Abe et al. | |
| 2015/0369799 A1 | 12/2015 | Miyazawa et al. | |
| 2018/0364231 A1 | 12/2018 | Gu et al. | |

FOREIGN PATENT DOCUMENTS

| EP | 1724582 A2 | 11/2006 |
|---|---|---|
| JP | H05153541 A | 6/1993 |

(Continued)

OTHER PUBLICATIONS

Extended European Search Report issued in the EP application No. 18777290.0 dated Dec. 18, 2020.
Reid, Scott M., et al. "Development of a rapid chromatographic strip test for the pen-side detection of foot-and-mouth disease virus antigen." Journal of virological methods 96.2 (2001): 189-202.
International Preliminary Report issued in corresponding International Application No. PCT/JP2018/012330, dated Oct. 1, 2019.
Written Opinion issued in corresponding International Application No. PCT/US2015/031278, dated Nov. 27, 2015, 6 pages.
First Office Action dated Nov. 2, 2022 in Chinese Application No. 201880021112.1 (English translation provided).

*Primary Examiner* — Jeffrey S Parkin
(74) *Attorney, Agent, or Firm* — Fox Rothschild LLP

(57) ABSTRACT

The purpose of the present invention is to: provide an agent that effectively suppresses inhibition of antigen-antibody reaction in an immunoassay using a sample containing a body fluid, in particular, a component derived from a biological mucosal membrane, such as saliva; and to suppress false positive and false negative results in the immunoassay. The present invention provides an agent for suppressing inhibition of immune reaction, characterized in that the agent comprises a compound of the following (1) or (2): (1) Sulfonic acid compound of the formula $R^1$—$SO_3H$ or a salt thereof. (In the formula, $R^1$ is selected from the group consisting of: a straight-chain $C_5$-$C_{30}$ alkyl group; a straight-chain $C_1$-$C_{30}$ alkyl group substituted with an aryl group having at least one straight-chain $C_5$-$C_{30}$ alkyl group; and an aryl group having at least one straight-chain $C_5$-$C_{30}$ alkyl group. These groups may include a substituent group); and (2) Quaternary ammonium ion of the formula $N^+$—$R^2R^3R^4R^5$ or a salt thereof. (In the formula, $R^2$—$R^5$ are each independently a straight-chain $C_1$-$C_{30}$ alkyl group, or an aryl group substituted with at least one straight-chain $C_5$-$C_{30}$ alkyl group. These groups may include a substituent group); wherein the agent is capable of suppressing immune reaction inhibitory action caused by a body fluid in an immunoassay sample.

14 Claims, 2 Drawing Sheets

(56) References Cited

FOREIGN PATENT DOCUMENTS

| | | | |
|---|---|---|---|
| JP | H06300761 A | 10/1994 |
| JP | H08139639 A | 5/1996 |
| JP | H10218136 A | 8/1998 |
| JP | 2002357599 A | 12/2002 |
| JP | 2003149244 A | 5/2003 |
| JP | 2003344413 A | 12/2003 |
| JP | 2005241415 A | 9/2005 |
| JP | 2005291783 A | 10/2005 |
| JP | 2009052945 A | 3/2009 |
| JP | 2010117244 A | 5/2010 |
| JP | 2010156576 A | 7/2010 |
| JP | 2011038903 A | 2/2011 |
| JP | 2011052971 A | 3/2011 |
| JP | 2012025749 A | 2/2012 |
| JP | 469245 B2 | 7/2012 |
| JP | 2014149189 A | 8/2014 |
| JP | 2017067513 A | 4/2017 |
| WO | 2011125873 A1 | 10/2011 |
| WO | 2017065261 A1 | 4/2017 |

\* cited by examiner

[FIG. 1]
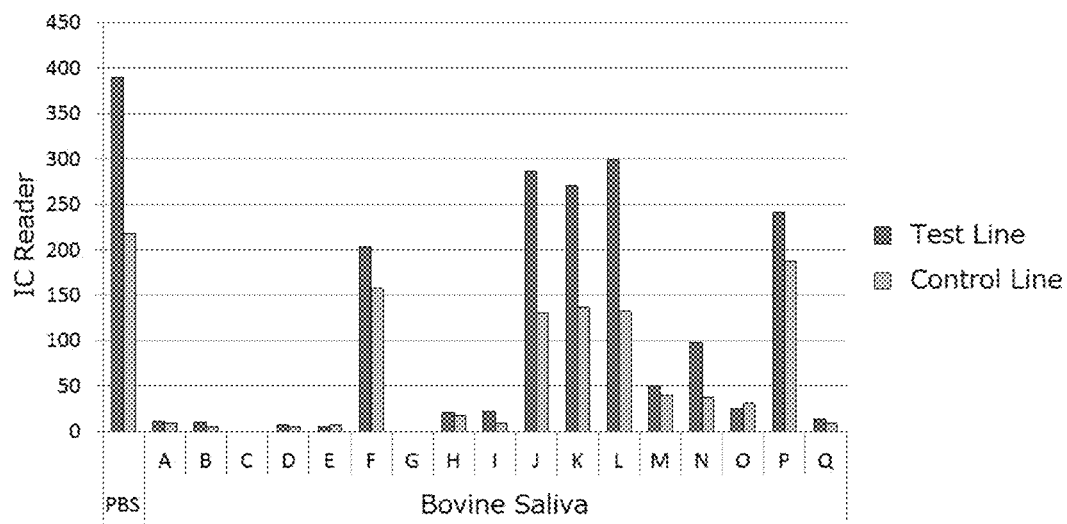
[FIG. 2]
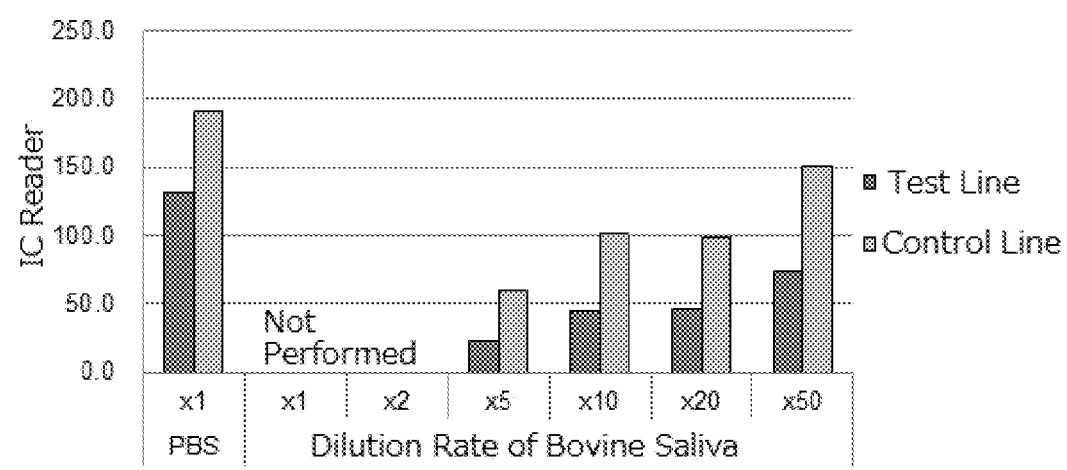

[FIG. 3]
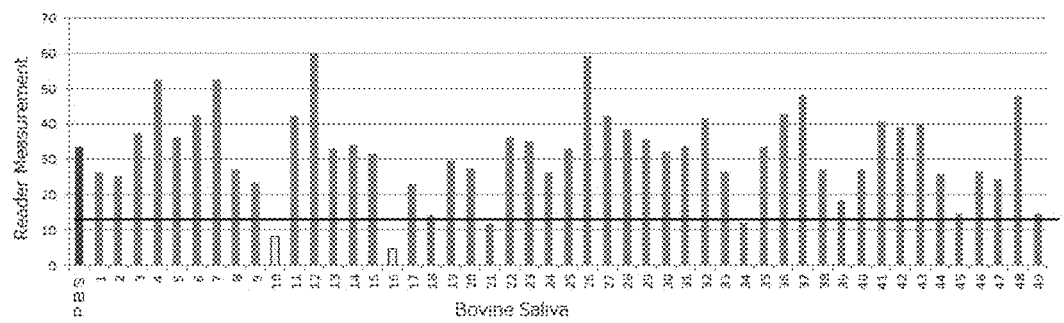

IMMUNOASSAY METHOD TO PREVENT INHIBITION OF ANTIGEN-ANTIBODY BINDING INTERACTIONS IN MUCOSAL FLUIDS

CROSS-REFERENCES TO RELATED APPLICATIONS

This application is a 35 U.S.C. § U.S. national entry of International Application Application PCT/JP2018/012330, having an International filing date of Mar. 27, 2010, which claims under 35 U.S.C. § 119 the benefit of Japanese Patent Application 2017-061335 filed Mar. 27, 2017. The entire contents of these applications are incorporated herein by reference in their entirety.

TECHNICAL FIELD

The present invention relates to provision of an inhibition suppressing substance for suppressing inhibition of antigen-antibody reaction by a body fluid component, in particular, a component derived from a biological mucosal membrane such as saliva in an immunoassay, and to an immunoassay that is rapid, simple, and accurate by using the inhibition suppressing substance.

BACKGROUND ART

Various simple test methods have currently been developed for diagnosing a disease or the like of humans and animals. As the simple diagnostic method, mainly a method of diagnosis by using a binding reaction (antigen-antibody reaction) of a specific antibody to a target substance (a pathogen or the like) to be detected, and an enzyme-linked immunosorbent assay (ELISA), an immunochromatography method, a latex agglutination method, or the like has been widely known. Since the results can be obtained rapidly and simply after collecting a sample from a patient or an infected animal, the treatment can be started in an early stage, and therefore, the importance of a simple test reagent and a kit has been increased year by year in the fields of medical care and animal husbandry.

At present, in the diagnosis of a disease in humans and livestock, practical use of a simple diagnostic method such as a method of rapid diagnosis by using a pharynx swab or the like collected from a patient as a sample has progressed in some of pathogens. However, this is limited to some scenes of rapid diagnosis of influenza, or the like, and a target that can be diagnosed is still limited.

As one of the factors, it can be mentioned that a body fluid component such as saliva derived from humans or animals, which is mixed into a sample, gives an adverse effect on the antigen-antibody reaction (false positive and false negative results), and there may be a case where a phenomenon not capable of obtaining the diagnostic result accurately is generated. For example, in foot-and-mouth disease that causes serious damage to livestock production, rapid diagnosis on the scene is important, and therefore, immunochromatography not requiring a large instrument is required, however, there has been a problem that due to the mixing of a component derived from a biological mucosal membrane such as bovine saliva into a sample, abnormal reaction of immunochromatography is generated, and accurate diagnosis cannot be performed.

Among body fluid samples, in particular, in a case of a sample derived from a biological mucosal membrane such as saliva, it has been known that host defense components derived from a mucosal immune system are contained in a large amount, and causes false positive and false negative results in the detection of a substance to be detected by immunoassay (Patent Documents 1 and 2).

Such a research and development of an inhibition suppressing substance for suppressing inhibition of antigen-antibody reaction by a body fluid component such as saliva has also been activated, and mainly, a technique for using substances having a surfactant activity such as various surfactants, or a polymer with a large molecular weight having a large number of ionic functional groups such as sulfonic acid groups, carboxyl groups, or sulfuric acid groups in the molecule has been attracting attention. For example, a technique for solubilizing aggregation of mutans *streptococcus* by mucin in saliva with a nonionic or amphoteric surfactant (Patent Document 3), a technique for pre-treating a sample derived from pharynx by using a cation exchange resin having a sulfonic acid group and/or a carboxyl group (Patent Document 4), a technique for suppressing action of an interfering substance in serum by an ionic surfactant including a polymer of hydrophobic cyclic monomers having a sulfonic acid group, a carboxylic acid group, or the like (Patent Document 5), a technique for suppressing action of an interfering substance in blood by a conjugated diene-based copolymer containing a sulfonic acid group or a salt thereof (Patent Document 6), a technique for suppressing interference action of IgA or the like in a component derived from a biological mucosal membrane by using dextran sulfate having two or more sulfuric acid groups and having an average molecular weight of 5,000 to 500,000 (Patent Document 1), and the like have been proposed. Further, in an example of using a low-molecular compound, a technique for suppressing an interfering substance in an immunological measurement of hemoglobin in a sample such as stool or saliva with a chemical substance having a SH group (Patent Document 7), and a method of treating a sample in the oral cavity such as saliva at the time of a measurement and identification test of dental caries-causing bacteria with an anionic surfactant such as sodium dodecyl sulfate (Patent Document 2) have been proposed. In addition, it has been described that in measuring a viral antigen in a sample derived from blood containing a virus such as hepatitis C virus (HCV), by using an anionic, amphoteric ionic, or nonionic surfactant-containing treatment solution, the antigen can be efficiency extracted from virus particles, and further measurement inhibition of a component in serum can be suppressed in the sample (Patent Document 8).

However, although in all of the techniques and the like described above, a certain effect has been achieved on a limited target antigen such as a specific pathogen, a potent suppressing agent against the inhibition in a wide range of antigen-antibody reactions by a body fluid component such as saliva has not been provided yet, and thus there has been a strong demand for the provision of a potent reaction inhibition suppressing agent that can be applied to the wide range of protein antigens and the whole various pathogens including the antigens.

CITATION LIST

Patent Document

Patent Document 1: JP 2014-149189 A
Patent Document 2: JP 2009-52945 A
Patent Document 3: JP 2002-357599 A
Patent Document 4: JP 4969245 B2
Patent Document 5: JP 2005-241415 A Patent Document 6: JP 9-304384 A
Patent Document 7: JP 2010-117244 A
Patent Document 8: JP 3171827 B2

SUMMARY OF THE INVENTION

Technical Problem

The present invention is to provide a simple and accurate immunoassay for not only specific pathogens but also widely common protein antigens, by using a body fluid sample, in particular, a sample derived from a biological mucosal membrane such as saliva, and further, is to provide a suppressing agent against the inhibition of antigen-antibody reaction by a body fluid component such as saliva that is used at that time.

Problems to be Solved by the Invention

In the present invention, in order to solve this problem, focusing attention on saliva that has strong immune reaction inhibitory action among body fluid components, it has been considered that a substance capable of suppressing strong immune reaction inhibitory action against a wide range of protein antigens derived from a saliva component can be a reaction inhibition suppressing agent capable of being applied to detection and measurement techniques for a wide range of pathogens and allergens.

In view of this, bovine saliva secreted in a large amount was collected from a large number of individuals, each of the immune reaction inhibitory activities was examined, and a saliva sample having the highest inhibitory activity was used to conduct screening experiment by using immunochromatography that can easily confirm the effect. As a target antigen to be detected at that time, a *Campylobacter* antigen was selected, and a *Campylobacter* detection kit available on the market was used.

First, previously, various surfactants with which a certain effect has been confirmed in immune reaction of a specific pathogen or the like by a body fluid sample such as saliva have been tried, but the effects of all of the surfactants have not been sufficient. Next, when various column resins have been tried, in particular, a strongly acidic cation exchange resin having a sulfonic acid group has had a high effect, but there has been a disadvantage that the effect was not stabilized, for example, the performance was deteriorated by drying.

Next, in order to examine the effect stabilization of the strongly acidic cation exchange resin having a sulfonic acid group, impurities of the resin were washed with a developing solution for immunochromatography, and the reactivity of the control line to the saliva sample was measured by using immunochromatography for detecting foot-and-mouth disease antigens. At the same time, similar measurement has been performed also for the washing solution after washing for comparison. As a result, surprisingly, the washing solution showed reactivity almost 10 times stronger than that of the resin after washing. That is, it is understood that the high effect of suppressing immune inhibition observed in the strongly acidic cation exchange resin having a sulfonic acid group was a low-molecular compound having a sulfonic acid group, generated during the production process of the strongly acidic cation exchange resin and mixed as an impurity.

In view of this, when the effect of suppressing reaction inhibition was evaluated for various low-molecular sulfonates that are likely to be mixed as impurities by measuring the reactivity of a control line for a saliva sample and the detection sensitivity to a foot-and-mouth disease virus, it has been found that an aliphatic or aromatic sulfonate with at least one straight-chain alkyl group having 5 or more carbon atoms exhibits a high effect of suppressing reaction inhibition, and can prevent the false positive and false negative results, in an immunoassay of various protein antigens.

Further, a low-molecular compound having a strong ionic functional group, similar to the sulfonate, was searched, and the similar effect of suppressing reaction inhibition was confirmed also for various quaternary ammonium salts.

In view of the above, it has been understood that aliphatic or aromatic sulfonic acid having at least one straight-chain $C_5$-$C_{30}$ alkyl group or a salt thereof, and a quaternary ammonium ion or a salt thereof can be used as a suppressing agent for inhibition of immune reaction by the mixture of a body fluid such as saliva in an immunoassay.

The findings described above have been obtained, and thus the present invention has been completed.

That is, the present invention is as follows.

[1] An agent for suppressing inhibition of immune reaction, characterized in that the agent comprises a compound of the following (1) or (2):

(1) a sulfonic acid compound of the formula $R^1$—$SO_3H$, or a salt thereof, wherein $R^1$ is selected from the group consisting of: a straight-chain $C_5$-$C_{30}$ alkyl group, a straight-chain $C_1$-$C_{30}$ alkyl group substituted with an aryl group having at least one straight-chain $C_5$-$C_{30}$ alkyl group, and an aryl group having at least one straight-chain $C_5$-$C_{30}$ alkyl group, wherein these groups may include a substituent group; and (2) a quaternary ammonium ion of the formula $N^+$—$R^2R^3R^4R^5$, or a salt thereof, wherein $R^2$ to $R^5$ are each independently a straight-chain $C_1$-$C_{30}$ alkyl group, or an aryl group substituted with at least one straight-chain $C_5$-$C_{30}$ alkyl group wherein these groups may include a substituent group;

wherein the agent is capable of suppressing immune reaction inhibitory action caused by a body fluid in an immunoassay sample.

In this regard, the expression "agent for suppressing inhibition of immune reaction" of the present invention is referred to as a compound significantly suppressing the immune reaction inhibitory action derived from a body fluid that is included in or may be included in a test sample, or a composition containing the compound as an active component, in an immunoassay using the antigen-antibody reaction for detecting or measuring a target antigen that may be present in a test sample.

[2] The agent described in the above [1], wherein in the formula of (1), $R^1$ is selected from the group consisting of: an unsubstituted straight-chain $C_5$-$C_{20}$ alkyl group, a straight-chain $C_1$-$C_{20}$ alkyl group substituted with a phenyl group having a straight-chain $C_5$-$C_{20}$ alkyl group, and a phenyl group substituted with a straight-chain $C_5$-$C_{20}$ alkyl group.

[3] The agent described in the above [1], wherein in the formula of (2), $R^2$ to $R^5$ are each independently a straight-chain $C_1$-$C_{20}$ alkyl group optionally substituted with an aryl group, or an aryl substituted with at least one straight-chain $C_5$-$C_{20}$ alkyl group.

[4] The agent described in the above [1], wherein in the formula of (2), $R^2$ to $R^5$ are each independently an unsubstituted straight-chain $C_1$-$C_{20}$ alkyl group, a straight-chain $C_1$-$C_{20}$ alkyl group substituted with a phenyl group, or a phenyl group substituted with a straight-chain $C_5$-$C_{20}$ alkyl group.

[5] The agent described in the above [4],
wherein in the formula of (2), $R^2$ to $R^5$ are defined as one of the following cases (a) to (e):
a case (a) where any one of $R^2$ to $R^5$ is a straight-chain $C_3$-$C_{20}$ alkyl group optionally substituted with a phenyl group, and the other three Rs are each a methyl group or an ethyl group;
a case (b) where any one of $R^2$ to $R^5$ is a methyl group or an ethyl group, and the other three Rs are each a straight-chain $C_3$-$C_{20}$ alkyl group optionally substituted with a phenyl group;
a case (c) where all of $R^2$ to $R^5$ are each a straight-chain $C_3$-$C_{20}$ alkyl group optionally substituted with a phenyl group;
a case (d) where any one of $R^2$ to $R^5$ is a benzyl group, and the other three Rs are each a straight-chain $C_3$-$C_{20}$ alkyl group optionally substituted with a phenyl group; and
a case (e) where any two of $R^2$ to $R^5$ are each a methyl group or an ethyl group, and the other two Rs are each a straight-chain $C_6$-$C_2M$ alkyl group optionally substituted with a phenyl group.

[6] The agent described in the above [5],
wherein in the formula of (2), $R^2$ to $R^5$ are defined as one of the following cases (a) to (e):
a case (a) where any one of $R^2$ to $R^5$ is a straight-chain $C_3$-$C_{16}$ alkyl group, and the other three Rs are each a methyl group;
a case (b) where any one of $R^2$ to $R^5$ is a methyl group, and the other three Rs are each a straight-chain $C_3$-$C_{12}$ alkyl group;
a case (c) where all of $R^2$ to $R^5$ are each a straight-chain $C_3$-$C_{12}$ alkyl group;
a case (d) where any one of $R^2$ to $R^5$ is a benzyl group, and the other three Rs are each a straight-chain $C_3$-$C_{12}$ alkyl group; and
a case (e) where any two of $R^2$ to $R^5$ are each a methyl group, and the other two Rs are each a straight-chain $C_3$-$C_{12}$ alkyl group.

[7] The agent described in any one of the above [1], and [3] to [6],
wherein the (2) is a salt of the ammonium ion,
wherein the salt is formed between the ammonium ion and a compound selected from the group consisting of hydrogen halide, nitric acid, hexafluorophosphoric acid, dihydrogen trifluoride, and perchloric acid.

[8] An immunoassay method, comprising a step of using the agent for suppressing inhibition of immune reaction in any one of the above [1] to [7].

More specifically, it can be said that a method for detecting or measuring a target antigen that is present in or may be present in a test sample by using a target antigen-specific antibody, comprising:
a process (a) of adding the agent for suppressing inhibition of immune reaction described in any one of the above [1] to [7]; and
a process (b) of bringing the test sample into contact with the target antigen-specific antibody,
wherein the process (a) is performed at the same time as or prior to the process (b), and in a case where the process (a) is performed prior to the process (b), the addition process is performed on at least one selected from the group consisting of a test sample-diluted solution, an antibody-diluted solution, a blocking solution, and a reaction buffer solution.

[9] An immunoassay method, comprising a step of using the agent for suppressing inhibition of immune reaction described in any one of the above [1] to [7],
wherein the immunoassay method measures a test substance in a sample containing a body fluid derived from a subject, in particular, a body fluid derived from a biological mucosal membrane of the subject, and is selected from the group consisting of an ELISA, an immunochromatography method, a Western blot method, an immunoblot method, an immunoprecipitation method, and a latex agglutination method,
Wherein the immunoassay method is capable of suppressing false positive and/or false negative result.

More specifically, it can be said that the method is a method of the following [9a], [9b], or [9c].

[9a] A method for detecting or measuring a target antigen by using an immunochromatography method, comprising:
a process (a) of adding the agent for suppressing inhibition of immune reaction described in any one of the above [1] to [7]; and
a process (b) of bringing the test sample into contact with an antibody for detecting the target antigen on a membrane,
wherein the process (a) is performed at the same time as or prior to the process (b), and in a case where the process (a) is performed prior to the process (b), the addition process is performed on at least one selected from the group consisting of a test sample-diluted solution, a developing solution for immunochromatography, an antibody-diluted solution, a blocking solution, a pre-treatment solution for a membrane for immunochromatography, a solution for immobilizing a conjugate pad, and a solution for immobilizing a sample pad.

[9b] A method for detecting or measuring a target antigen by using an ELISA, comprising:
a process (a) of adding the agent for suppressing inhibition of immune reaction described in any one of the above [1] to [7]; and
a process (b) of bringing the test sample into contact with an antibody for detecting the target antigen,
wherein the process (a) is performed at the same time as or at a different time from the process (b), and in a case where the process (a) is performed at a different time from the process (b), the addition process is performed on at least one selected from the group consisting of a test sample-diluted solution, a blocking solution, a primary antibody-diluted solution, a secondary antibody-diluted solution, and a buffer solution for washing.

[9c] A method for detecting or measuring a target antigen by using any method selected from a Western blot method, an immunoblot method, an immunoprecipitation method, and a latex agglutination method, comprising:
a process (a) of adding the agent for suppressing inhibition of immune reaction described in any one of the above [1] to [7]; and
a process (b) of bringing the test sample into contact with an antibody for detecting the target antigen,
wherein the process (a) is performed at the same time as or prior to the process (b), and in a case where the process (a) is performed prior to the process (b), the addition process is performed on at least one selected from the group consisting of a test sample-diluted solution, a blocking solution, an antibody-diluted solution, and a reaction buffer.

[10] The method described in the above [9],
wherein the sample containing a body fluid derived from a subject contains at least one body fluid derived from a biological mucosal membrane selected from the group consisting of saliva, sputum, a throat swab, a nasal swab, a nasal aspirate, and a keratoconjunctive swab.

[11] The method described in any one of the above [8] to [10], wherein the test substance is a substance selected from the group consisting of a pathogen, a pathogenic microorganism, a hormone, an inflammation-related substance, a prostaglandin, and a metabolic syndrome-related substance.

[12] The method described in the above [11], wherein the pathogen or the pathogenic microorganism is a pathogen or a pathogenic microorganism, selected from the group consisting of a foot-and-mouth disease virus, an influenza virus, an adenovirus, a RS virus, a coronavirus, a rabies virus, a *Bordetella pertussis*, a hemolytic *streptococcus*, an *E. coli*, a food poisoning bacterium, a *Chlamydia trachomatis*, and a *mycoplasma*.

[13] A kit for immunoassay, comprising the agent for suppressing inhibition of immune reaction described in any one of the above [1] to [7].

[14] The kit described in the above [13], wherein the kit for immunoassay is a kit for any immunoassay selected from the group consisting of an ELISA, an immunochromatography method, a Western blot method, an immunoblot method, an immunoprecipitation method, and a latex agglutination method.

[15] A kit for diagnosing whether or not a subject suffers from a pathogenic disease by immune reaction using a body fluid derived from the subject, in particular, a body fluid derived from a biological mucosal membrane of the subject, comprising the agent for suppressing inhibition of immune reaction described in any one of the above [1] to [7], and at least one of a diluent for the body fluid sample to be tested, a developing solution, and a blocking solution.

[16] The kit described in the above [15], wherein the pathogenic disease is a disease caused by a pathogen or a pathogenic microorganism, selected from the group consisting of a foot-and-mouth disease virus, an influenza virus, an adenovirus, a RS virus, a coronavirus, a rabies virus, a *Bordetella pertussis*, a hemolytic *streptococcus*, an *E. coli*, a food poisoning bacterium, a *Chlamydia trachomatis*, and a *mycoplasma*.

Effects of the Invention

By using the agent for suppressing inhibition of immune reaction according to the present invention as a pre-treatment solution or a developing solution in various immunoassay methods, the deterioration of antigen-antibody reaction can be efficiently suppressed even for a body fluid sample such as saliva or a test sample to which saliva or the like may be mixed. Conventionally, pre-treatment or the like has been required for removing the influence of a body fluid such as saliva, however, according to the present invention, it becomes possible to measure a sample into which a body fluid such as saliva may be mixed without performing pretreatment or the like, and therefore, prompt and accurate response becomes possible in the field of medical care or animal husbandry, and it is expected to contribute to the improvement of the quality of test and the improvement of the productivity.

In particular, diagnosis of an important disease such as foot-and-mouth disease or influenza virus disease becomes possible to perform accurately in disease diagnosis of livestock such as bovine, and swine by using a rapid and simple kit for immunochromatography even for a test sample having a strong immune reaction inhibitory activity such as saliva or a nasal and throat swab.

BRIEF DESCRIPTION OF DRAWINGS

FIG. 1 is verification of the inhibitory activity in bovine saliva for immunochromatography. When a *Campylobacter* positive sample was tested in NH Immunochromato *Campylobacter*, which is immunochromatography for detecting *Campylobacter*, the influence on the test line (reaction inhibition in detecting *Campylobacter* with an anti-*Campylobacter* antibody), and the influence on the control line (reaction inhibition in detecting an anti-*Campylobacter* disease antibody with an anti-IgG antibody).

FIG. 2 is verification of the recoverability of reactivity by diluting a bovine saliva sample in immunochromatography for detecting *Campylobacter* (NH Immunochromato *Campylobacter*).

FIG. 3 is verification of the suppressive effect on immune reaction inhibition of a straight-chain alkylsulfonic acid salt by using immunochromatography for detecting foot-and-mouth disease antigens. Detection test results of foot-and-mouth disease viruses in 49 samples of bovine saliva, in which 0.3 (w/v) % of straight-chain sodium dodecylbenzenesulfonate was added.

DESCRIPTION OF EMBODIMENTS

1. Agent for Suppressing Inhibition of Immune Reaction According to the Present Invention (1-1) Compound Used as Agent for Suppressing Inhibition of Immune Reaction According to the Present Invention In the present invention, the expression "agent for suppressing inhibition of immune reaction" refers to a compound that suppresses the immune reaction inhibitory action derived from a body fluid that is included (or may be included) in a test sample, in particular, a body fluid derived from a biological mucosal membrane, or a composition containing the compound as an active component, in an immunoassay using the antigen-antibody reaction for detecting or measuring a target antigen that may be present in a test sample.

One of the agents for suppressing inhibition of immune reaction according to the present invention is an aliphatic or aromatic sulfonic acid having a straight-chain $C_5$ or more alkyl group that may be optionally substituted in the molecule, or a salt thereof.

Another one is a quaternary ammonium ion having a straight-chain $C_3$ or more alkyl group that may be optionally substituted in the molecule, or a salt thereof. Both are characterized by being a low-molecular compound that has a large bias of electric charges in the molecule.

(1-2) Straight-Chain Alkyl Group-Containing Sulfonic Acid Compound or Salt Thereof Among the agents for suppressing inhibition of immune reaction according to the present invention, the straight-chain alkyl group-containing sulfonic acid compound has at least one straight-chain $C_5$-$C_{30}$ alkyl group that may be optionally substituted in the molecule, and is a sulfonic acid compound of the following (formula 1), or a salt thereof.

$$\text{"}R^1\text{—}SO_3H\text{"} \qquad \text{(Formula 1)}$$

(in the formula, $R^1$ is a straight-chain $C_5$-$C_{30}$ alkyl group, a straight-chain $C_1$-$C_{30}$ alkyl group substituted with a carbocyclic aromatic group having at least one $C_5$-$C_{30}$ alkyl group, or a carbocyclic aromatic group having at least one straight-chain $C_5$-$C_{30}$ alkyl group, and these groups may include a substituent group.)

That is, the straight-chain alkyl group-containing sulfonic acid compounds are as follows:

(a) a straight-chain $C_5$-$C_{30}$ alkyl sulfonic acid, preferably a straight-chain $C_7$-$C_{20}$ alkyl sulfonic acid, more preferably a straight-chain $C_8$-$C_{15}$ alkyl sulfonic acid, and particularly preferably a straight-chain $C_{10}$-$C_{12}$ alkyl sulfonic acid, each of which may be optionally substituted, or a salt thereof;

(b) a carbocyclic aromatic (aryl) sulfonic acid having a straight-chain $C_5$-$C_{30}$ alkyl group, preferably a straight-chain $C_7$-$C_{20}$ alkyl group, more preferably a straight-chain $C_8$-$C_{15}$ alkyl group, and particularly preferably a straight-chain $C_{10}$-$C_{12}$ alkyl group, each of which may be optionally substituted, or a salt thereof; and (c) a straight-chain $C_1$-$C_{30}$ alkyl sulfonic acid, preferably a straight-chain $C_1$-$C_{20}$ alkyl sulfonic acid, more preferably a straight-chain $C_1$-$C_{15}$ alkyl sulfonic acid, and particularly preferably a straight-chain $C_1$-$C_{12}$ alkyl sulfonic acid, with a carbocyclic aromatic (aryl) group having a straight-chain $C_5$-$C_{30}$ alkyl group, preferably a straight-chain $C_7$-$C_{20}$ alkyl group, more preferably a straight-chain $C_8$-$C_{15}$ alkyl group, and particularly preferably a straight-chain $C_{10}$-$C_{12}$ alkyl group, each of which may be optionally substituted, or a salt thereof.

As for the straight-chain $C_5$-$C_{30}$ alkyl group, the effect of suppressing reaction inhibition tends to be higher as the number of carbon atoms is larger, but the length of the number of carbon atoms is limited from the viewpoint of the ease of production and the ease of dissolution into a sample for measurement.

As the carbocyclic aromatic group (aryl group), a phenyl group, or a naphthyl group is preferred, and a phenyl group is particularly preferred.

These straight-chain alkyl group-containing sulfonic acid compounds may have a substituent group other than a straight-chain alkyl group. As the substituent group, any substituent group can be accepted as long as it is a functional group capable of substituting an alkyl group, such as a halogen molecule, a hydroxy group, an alkenyl group, a cycloalkyl group, a cycloalkenyl group, an alkoxyl group, an acyl group, an acetyl group, a formyl group, a carbonyl group, a carboxyl group, an amino group, an imino group, a cyano group, an azo group, a nitro group, a thiol group, or a ketone group, and a functional group that does not impair the bias of electric charges in the molecule of the entire straight-chain alkyl group-containing sulfonic acid compound is preferred. Specifically, a functional group having a positive charge, or no electric charge is preferred.

As a representative example of the straight-chain alkyl group-containing sulfonic acid compound, a straight-chain alkyl sulfonic acid such as 1-pentanesulfonic acid, 1-hexanesulfonic acid, 1-heptanesulfonic acid, 1-octanesulfonic acid, 1-nonanesulfonic acid, 1-decanesulfonic acid, 1-undecanesulfonic acid, or 1-dodecylsulfonic acid; or a straight-chain alkylbenzene sulfonic acid such as 1-dodecylbenzenesulfonic acid, p-octylbenzenesulfonic acid, or p-toluenesulfonic acid can be mentioned, however, the straight-chain alkyl group-containing sulfonic acid compound is not limited thereto.

Further, the salt of the straight-chain alkyl group-containing sulfonic acid refers to a salt obtained by neutralizing a sulfo group (sulfonic acid group) with a base compound such as an alkali metal compound, an alkaline earth compound, or ammonia. As the salt, preferably, a sodium salt, a potassium salt, a calcium salt, a magnesium salt, an ammonium salt, and the like are mentioned, and in particular, a sodium salt is preferred.

(1-3) Quaternary Ammonium Ion or Salt Thereof

Among the agents for suppressing inhibition of immune reaction according to the present invention, the quaternary ammonium ion or a salt thereof is a quaternary ammonium cation having always a positive charge of the following (formula 2) and having at least any one group of a straight-chain alkyl group that may be optionally substituted or an aryl group that may be optionally substituted, in the molecule, or a quaternary ammonium salt that is a salt with an anion of halogen or the like.

A quaternary ammonium ion of (Formula 2)

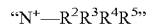

(In the formula, $R^2$ to $R^5$ each independently represent a straight-chain $C_1$-$C_{30}$ alkyl group, or a carbocyclic aromatic group substituted with at least one straight-chain $C_5$-$C_{30}$ alkyl group, and these groups may have a substituent group), or a salt thereof.

In this regard, it is preferred that at least one group of the independent $R^2$ to $R^5$ is (i) a straight-chain $C_3$-$C_{30}$ alkyl group, preferably a straight-chain $C_3$-$C_{20}$ alkyl group, and more preferably a straight-chain $C_5$-$C_{15}$ alkyl group, or (ii) a straight-chain $C_1$-$C_{30}$ alkyl group, preferably a straight-chain $C_3$-$C_{20}$ alkyl group, and more preferably a straight-chain $C_5$-$C_{15}$ alkyl group, each of which has a carbocyclic aromatic group (aryl group) that is substituted with a straight-chain $C_3$-$C_{30}$ alkyl group, preferably a straight-chain $C_3$-$C_{20}$ alkyl group, and more preferably a straight-chain $C_5$-$C_{15}$ alkyl group as a substituent group.

Further, as the carbocyclic aromatic group (aryl group), a phenyl group, or a naphthyl group is preferred, and a phenyl group is particularly preferred.

In a desirable embodiment of the present invention, $R^2$ to $R^5$ can be represented as any case of the following (a) to (e):

a case (a) where any one of $R^2$ to $R^5$ is a straight-chain $C_3$-$C_{20}$ alkyl group, and preferably a straight-chain $C_3$-$C_{16}$ alkyl group, each of which may be optionally substituted with a phenyl group, and the other three Rs are each a methyl group or an ethyl group, and preferably an methyl group;

a case (b) where any one of $R^2$ to $R^5$ is a methyl group or an ethyl group, and preferably a methyl group, and the other three Rs are each a straight-chain $C_3$-$C_{20}$ alkyl group, and preferably a straight-chain $C_3$-$C_{12}$ alkyl group, each of which may be optionally substituted with a phenyl group;

a case (c) where all of $R^2$ to $R^5$ are each a straight-chain $C_3$-$C_{20}$ alkyl group optionally substituted with a phenyl group, and preferably an unsubstituted straight-chain $C_3$-$C_{12}$ alkyl group;

a case (d) where any one of $R^2$ to $R^5$ is a benzyl group, and the other three Rs are each a straight-chain $C_3$-$C_{20}$ alkyl group optionally substituted with a phenyl group, and preferably an unsubstituted straight-chain $C_3$-$C_{12}$ alkyl group; and a case (e) where any two of $R^2$ to $R^5$ are each a methyl group or an ethyl group, and preferably a methyl group, and the other two Rs are each a straight-chain $C_6$-$C_{20}$ alkyl group optionally substituted with a phenyl group, and preferably an unsubstituted straight-chain $C_3$-$C_{12}$ alkyl group.

The quaternary ammonium ion or a salt thereof used as the agents for suppressing inhibition of immune reaction according to the present invention may have a substituent group other than a straight-chain alkyl group. As the substituent group, any substituent group can be accepted as long as it is a functional group capable of substituting an alkyl group, such as a halogen molecule, a hydroxy group, an alkenyl group, a cycloalkyl group, a cycloalkenyl group, an alkoxyl group, an acyl group, an acetyl group, a formyl group, a carbonyl group, a carboxyl group, an amino group, an imino group, a cyano group, an azo group, a nitro group, a thiol group, or a ketone group, and a functional group that does not impair the bias of electric charges in the molecule of the entire quaternary ammonium ion is preferred. Specifically, a functional group having a negative charge, or no electric charge is preferred.

Representative examples of the quaternary ammonium ion include n-octyltrimethylammonium, lauryl trimethylammonium, myristyl trimethylammonium, stearyl trimethylammonium, dodecyl trimethylammonium, methyl trioctylammonium, methyl tributylammonium, tetrabutylammonium, tetramethylammonium, and benzyl tributylammonium, however, the quaternary ammonium ion is not limited to these ammonium ions.

The quaternary ammonium ion used as the agents for suppressing inhibition of immune reaction according to the present invention is always positively charged and highly reactive, and therefore, the quaternary ammonium ion is preferably used as a stable ammonium salt. As the anion that forms a stable ammonium salt, halogen, nitric acid, hexafluorophosphoric acid, dihydrogen trifluoride, perchloric acid, or the like is mentioned, and a halide of Cl, Br, I, or the like is preferred.

2. Detection and Measurement Target in Immunoassay of the Present Invention (2-1) Detection and Measurement Target The detection substance in the present invention is an antigen or an antibody, which can be measured by an immunoassay method using an antigen-antibody reaction, such as an immunoassay. As the antigen, any antigen is accepted as long as it can produce an antibody, and a protein, a glycoprotein, or a peptide is preferred, and a protozoan, a fungus, a bacterium, a *mycoplasma*, a *rickettsia, Chlamydia*, a virus, and the like, each of which contains such a substance, can also be detected. In particular, the immunoassay is preferably applied in rapidly and accurately detecting and quantifying a pathogenic virus or bacterium, for example, a foot-and-mouth disease virus, an influenza virus, an adenovirus, a respiratory syncytial (RS) virus, a coronavirus, a rabies virus, *Bordetella pertussis*, a hemolytic *streptococcus*, or a food poisoning bacterium such as *Campylobacter, Salmonella*, and pathogenic *Escherichia coli*.

Further, the immunoassay is also useful in detecting and measuring an eicosanoid such as a prostaglandin from a saliva sample, a stress hormone such as cortisol, a sex hormone such as testosterone, or estradiol, various hormones such as melatonin, and insulin, an inflammation-related substance such as TNF-α, or IL-1β, a digestive enzyme such as α-amylase, and a metabolic syndrome-related substance such as adiponectin by an ELISA, an immunoassay (enzyme immunosorbent assay (EIA)), or the like (the Bulletin of University of Kochi, edited by Faculty of Nursing, Vol. 64, pp. 73-83, 2014).

In addition, in quality control of food and drink, feed, and the like, in a case where there is a possibility of contamination by a body fluid of humans or animals during storage, the immunoassay can also be applied to the detection or quantification of an allergen protein antigen in food and drink, and feed.

As the antibody for detecting the antigen, not even a monoclonal antibody, but a polyclonal antibody, or an antiserum can also be used as long as it is an antibody that specifically reacts with and binds to the antigen to be measured.

(2-2) Test Sample

The test sample to be subjected to the immunoassay of the present invention is a sample that has or may have a target antigen or a target antibody, and is not particularly limited, however, as the test sample, a biological sample that can significantly exert the effects of the present invention of suppressing the influence of an interfering substance, in particular, a sample derived from a biological mucosal membrane such as saliva is preferred, and typically, a body fluid derived from a biological mucosal membrane, which is collected from humans and animals (livestock such as swine, bovines, chickens, goats, and sheep, pet animals such as dogs and cats, and the like), for example, a sample selected from saliva, an oral swab, sputum, a pharynx swab, a nasal swab, a nasal aspirate, a keratoconjunctive swab, or the like, or a dilute solution thereof can be mentioned. In addition, food and drink, feed, and the like, which have a possibility of contamination by such a body fluid, can also be test samples. In particular, a saliva sample is preferred because of being collected by the most non-invasive collection method.

3. Immunoassay of the Present Invention and Use Method of Agent for Suppressing Inhibition of Immune Reaction of the Present Invention (3-1) Detection System and Measurement System, by Using Antigen-Antibody Reaction of the Present Invention The agent for suppressing inhibition of immune reaction according to the present invention can be applied to any system as long as the system is a detection system or a measurement system, which uses antigen-antibody reaction. Specifically, when the agent for suppressing inhibition of immune reaction is applied to immunochromatography, an ELISA, Western blotting, immunoblotting, immunoprecipitation, a latex agglutination method, or the like, false positive and false negative results are suppressed, and therefore, this is preferred. Especially, the agent for suppressing inhibition of immune reaction is highly effective when applied to the immunochromatography method that is easily affected by a substance derived from a mucosal membrane such as saliva.

Hereinafter, each immunoassay will be described in brief by way of typical use methods of the present invention, however, the use method of the present invention is not limited to these methods.

(a) Use Method in Immunochromatography Method

In an immunochromatography method, antibodies (capture antibodies) specific to a target antigen in a test sample are immobilized in advance on an appropriate membrane such as a nitrocellulose membrane, and antibodies labeled with metal colloid or the like prepared in a sample-dropping part, and immune complexes formed with the antigens in the sample are moved and developed using a capillary phenomenon of the membrane. The labeled amount (test line) when the immune complexes are trapped on the capture antibodies can be determined qualitatively by visual observation. The reactivity can also be quantified by using an immunochromatographic reader (hereinafter also referred to as an IC reader) as a reading device. Anti-IgG antibodies and the like that recognize an antibody labeled with metal colloid are immobilized on the downstream side of the immobilized capture antibodies, and the position to which the excessive antibodies labeled with metal colloid bind is confirmed visually or by an immunochromatographic reader as a control line.

In an immunochromatography method, a test sample is used as a solution of the test sample diluted with a buffer solution or the like, and the agent for suppressing inhibition of immune reaction according to the present invention is added in advance into the diluting solution, or can be added to the diluting solution together with the test sample.

At that time, as the diluting solution, when a Tris buffer solution, a phosphate buffer solution, or the like (to which a surfactant or a protein such as albumin may be added as needed), which is used as a common developing solution for immunochromatography method, is used, such a solution can be used as it is as a developing solution for immunochromatography method.

Further, the agent for suppressing inhibition of immune reaction according to the present invention can also be added in advance into a diluting solution of metal colloid-labeled antibodies, latex particle-labeled antibodies, or the like. The agent for suppressing inhibition of immune reaction according to the present invention may be used for blocking of latex particles.

In addition, the agent for suppressing inhibition of immune reaction according to the present invention can also be used in a membrane pre-treatment solution for blocking a membrane such as a nitrocellulose membrane used in an immunochromatography method, or in a solution for the immobilization on a conjugate pad or a sample pad.

That is, it can be said that the method for detecting or measuring a target antigen by using an immunochromatography method among the immunoassays of the present invention is a method including:

a process (a) of adding the agent for suppressing inhibition of immune reaction according to the present invention; and a process (b) of bringing a test sample into contact with an antibody for detecting a target antigen on a membrane, in which the process (a) is performed at the same time as or prior to the process (b), and in a case where the process (a) is performed prior to the process (b), the addition process is performed on at least one selected from the group consisting of a test sample-diluted solution, a developing solution for immunochromatography, an antibody-diluted solution, a blocking solution, a pre-treatment solution for a membrane for immunochromatography, a solution for immobilizing a conjugate pad, and a solution for immobilizing a sample pad.

In an immunoassay such as an immunochromatography method, the most suitable concentration range of the agent for suppressing inhibition of immune reaction according to the present invention to be added into a diluting solution, an pre-treatment solution or the like differs depending on the type of the agent for suppressing inhibition of immune reaction, the type of the organism to be tested, the age, the type of the body fluid to be mixed, the type of the target antigen to be detected, or the like, however, is generally 0.01 to 10 (w/v) %, preferably 0.02 to 5.0 (w/v) %, furthermore preferably 0.05 to 3.0 (w/v) %, and particularly preferably 0.1 to 1.0 (w/v) %.

(b) ELISA

If the ELISA is a direct adsorption method, a test sample solution is adsorbed to a solid phase of a microplate, glass beads, or the like, the solid phase is blocked with a protein (skim milk, albumin, or the like) that is not involved in the antigen-antibody reaction and the enzyme reaction, and then a target antigen-specific antibody is reacted to cause an antigen-antibody reaction, and the excessive antibodies are washed away (If the antibody is not labeled, an enzyme-labeled secondary antibody is reacted, and a washing process for the secondary antibody is added). Next, a substrate of labeled enzymes is added to detect the enzyme reaction product.

If the ELISA is a sandwich method, capture antibodies specific to a target antigen are adsorbed to a solid phase, the resultant solid phase is subjected to a blocking process, and then an antigen-specific antibody (primary antibody) that recognizes an epitope different from the epitopes of the test sample solution and the capture antibody is reacted, and if the primary antibody is not labeled, a labeled secondary antibody is further reacted.

Even in the directly adsorption method or the sandwich method, the agent for suppressing inhibition of immune reaction according to the present invention can be used by being added into a test sample-diluted solution or a solution of skim milk or the like for blocking, in an ELISA, and/or a diluting solution for antibodies such as target antigen-specific antibodies, and secondary antibodies.

That is, it can be said that the method for detecting or measuring a target antigen by using an ELISA among the immunoassays of the present invention is a method including:

a process (a) of adding the agent for suppressing inhibition of immune reaction according to the present invention; and a process (b) of bringing a test sample into contact with an antibody for detecting a target antigen, in which the process (a) is performed at the same time as or at a different time from the process (b), and in a case where the process (a) is performed at a different time from the process (b), the addition process is performed on at least one selected from the group consisting of a test sample-diluted solution, a blocking solution, a primary antibody-diluted solution, a secondary antibody-diluted solution, and a buffer solution for washing.

(c) Use Method in Other Immunoassays

Additionally, as the immunoassay in which the agent for suppressing inhibition of immune reaction according to the present invention is preferably used, there is an immunoagglutination method. The immunoagglutination method is a method of detecting or quantifying antigens or antibodies in a test sample, on the basis of the changes in the optical properties such as turbidity and absorbance of a reaction mixture, which are caused by antigen-antibody reaction, and also includes an immunoturbidimetric method, and a latex agglutination method by using latex particles. A test sample is added into a reaction mixture containing a labeled antiserum, or into a reaction mixture in which latex particles coated with antibodies specific to a target antigen are suspended, and the changes in the turbidity and the absorbance are observed and measured by aggregation of the antiserum or the latex particles due to the formation of immune complexes.

In addition to the addition into the test sample-diluted solution or the like at that time, the agent for suppressing inhibition of immune reaction according to the present invention can also be used in a solution for blocking latex particles or a reaction mixture.

In addition, in a Western blot method, the agent for suppressing inhibition of immune reaction according to the present invention can be added into an antibody-diluted solution, or a blocking solution, in addition to the test sample-diluted solution, and is added into an antibody-diluted solution, or a reaction buffer solution, in addition to the test sample-diluted solution, also in the immunoprecipitation method.

That is, other immunoassays are characterized by including a process of adding the agent for suppressing inhibition of immune reaction according to the present invention in at least one of the processes of preparing a test sample-diluted solution, an antibody-diluted solution, a blocking solution, and a reaction buffer solution, and/or a process of reacting a test sample with a target antigen-specific antibody.

More specifically, it can be said that the method for detecting or measuring a target antigen by using any method selected from a Western blot method, an immunoblot method, an immunoprecipitation method, and a latex agglutination method is a method including:

a process (a) of adding the agent for suppressing inhibition of immune reaction according to the present invention; and a process (b) of bringing a test sample into contact with an antibody for detecting a target antigen, in which the process (a) is performed at the same time as or prior to the process (b), and in a case where the process (a) is performed prior to the process (b), the addition process is performed on at least one selected from the group consisting of a test sample-diluted solution, a blocking solution, an antibody-diluted solution, and a reaction buffer.

(3-2) Kit for Immunoassay

The agent for suppressing inhibition of immune reaction according to the present invention can be combined with a common kit for various immunoassays to form a kit of the agent for suppressing inhibition of immune reaction according to the present invention. Further, in the kit, by including a container which is packed in advance with the agent for suppressing inhibition of immune reaction according to the present invention dissolved at a predetermined concentration in at least one solution of a buffer solution for dilution, a developing solution, a reaction mixture, a blocking solution, and the like, which are to be used in these various kits for immunoassay, the convenience can be more improved.

EXAMPLES

Hereinafter, the present invention will be described in more detail by way of Examples, however, the present invention is not limited by these Examples.

Other terms and concepts in the present invention are on the basis of the meanings of terms conventionally used in the field, and various techniques to be used to perform the present invention can be easily and reliably performed by those skilled in the art on the basis of known document and the like particularly except for the techniques that clearly indicated the source. Further, the various analyses and the like were conducted according to the methods described in instruction manuals, catalogs, and the like for the analytical instrument, the reagent, and the kit, which were used.

Note that the contents of the conventional art documents, patent publications, and patent applications cited in the present specification are referred to as the contents of the present invention.

(Example 1) Immune Reaction Inhibition by Saliva (1-1) Detection Inhibition of *Campylobacter* Antigen by Saliva In the present Example, in order to observe the inhibition of antigen-antibody reaction in immunochromatography for detecting *Campylobacter*, a sample, which is prepared by adding a *Campylobacter* (*Campylobacter jejuni*, ATCC 29428) killed culture into a sample-diluted solution obtained by diluting bovine saliva with a developing solution so as to be $8 \times 10^6$ cfu/mL, and stirring the resultant mixture, was added dropwise into immunochromatography for detecting *Campylobacter* (NH Immunochromato *Campylobacter*, manufactured by NH Foods Ltd.), and the test line and control line were measured by an immunochromatographic reader ($C_{10066}$, manufactured by Hamamatsu Photonics K.K.) (FIG. 1). The test line was coated with anti-*Campylobacter* antibodies, and the control line was coated with anti-mouse IgG antibodies, and the test line and the control line respond to a *Campylobacter* bacterial cell, and to an anti-*Campylobacter* antibody, respectively.

As a result, among the examined bovine saliva samples, the degree of inhibition of each sample differed depending on each individual from which the bovine saliva was derived, however, it was confirmed that the reaction was decreased in a case where bovine saliva was used as a sample as compared with that in a case where phosphate-buffered saline (PBS) of control was used as a sample. Further, it was also observed that the degree of the inhibition exerted even against the antigen-antibody reactions of which the combinations of antigen and antibody were completely different from each other was hardly changed.

Therefore, the saliva that exhibited strong inhibitory action in the present sample was selected as an examination sample for searching a substance suppressing the inhibitory activity.

(1-2) State of Inhibition by Bovine and Swine Saliva Against *Campylobacter* Antigen In this Example, it was confirmed that the state of inhibition by saliva for the similar immunoassay of *Campylobacter* antigen protein as in (1-1) was present not only in bovine saliva but also in swine saliva.

Specifically, bovine saliva and swine saliva were diluted with PBS by 10 times, and the obtained diluted solution was subjected to NH Immunochromato *Campylobacter* (manufactured by NH Foods Ltd.). In bovine saliva, in 20 samples, two samples showed false negative results in which the control line was inhibited, and one sample showed a false positive result, but in swine saliva, in 54 samples, there were zero samples that showed a false negative result, and 12 samples showed false positive results (Table 1).

In this regard, since the possibility of the presence of *Campylobacter* in a high concentration in the oral cavity was low, a case where the measurement value showed a high value on the test line was counted as a false positive result. Further, it was considered that there was a high possibility that the test line showed a false negative result for the saliva in which the control line was inhibited.

Some of the details of the results are shown in (Table 2).

TABLE 1

|  | Number of subject samples | Saliva in which the control line was inhibited | Saliva in which the (false) positive line was showed on the test line |
|---|---|---|---|
| Bovine Saliva | 20 | 2 | 1 |
| Swine Saliva | 54 | 0 | 12 |

TABLE 2

※Details of the results (Partial)

| Bovine Saliva (Sample Name, Breed, Sex, Age) | Test line Visual Observation | IC Reader | Control Line | Swine Saliva (Sample Name) | Test line Visual Observation | IC Reader | Control Line |
|---|---|---|---|---|---|---|---|
| BS-K1, Hybrid, Castrated ♂, 2 years and 3 months old | – | 5.3 | 99.9 | SS-K1 | – | 0.0 | 211.8 |
| BS-K2, Hybrid, ♀, 2 years and 3 months old | – | 6.0 | 62.7 | SS-K3 | – | 0.0 | 220.4 |
| BS-K2, Hybrid, ♀, 2 years and 5 months old | – | 6.1 | 103.1 | SS-K5 | – | 1.9 | 238.0 |
| BS-K7, Black, Castrated ♂, 2 years and 6 months old | – | 6.8 | 84.2 | SS-K10 | – | 1.3 | 234.4 |
| BS-K8, Hybrid, ♀, 1 year and 4 months old | – | 1.5 | 224.8 | SS-K44 | + | 150.8 | 264.7 |
| BS-K9, Black, Castrated ♂, 2 years and 4 months old | – | 0.6 | 7.0 | SS-K49 | – | 1.9 | 266.4 |
| BS-K10, Black, Castrated ♂, 2 years and 7 months old | + | 43.7 | 178.5 | SS-K53 | + | 114.7 | 303.2 |
| BS-K14, Black, Castrated ♂, 1 year and 4 months old | – | 3.4 | 245.9 | SS-K55 | – | 1.6 | 269.3 |
| BS-K15, Black, ♀, 1 year and 4 months old | – | 2.2 | 377.7 | SS-K61 | + | 210.2 | 205.8 |
| BS-K16, Hybrid, ♀, 1 year and 5 months old | – | 0.0 | 0.0 | SS-K83 | – | 3.4 | 296.3 |

(1-3) Reaction Inhibition by Saliva for Various Immunochromatography

In the present Example, by using a saliva sample (G) having the highest inhibitory activity obtained in Example (1-1), the degree of the immune reaction inhibition due to the contamination by saliva components to various immunochromatography in which the antigen proteins to be detected were different from each other was observed.

Specifically, an egg, a milk, or a wheat protein, which is an allergen protein of food, was selected as the model for immunochromatography for detecting different antigen proteins, an enterohemorrhagic *Escherichia coli* O157 was selected as the model for detecting a pathogen, and a foot-and-mouth disease virus was selected as the model for detecting a pathogenic virus, and the models were subjected to experiments by using "FASTKIT Slim Egg" (manufactured by NH Foods Ltd.), "FASTKIT Slim Wheat" (manufactured by NH Foods Ltd.), "NH Immunochromato O157" (manufactured by NH Foods Ltd.), and "immunochromatography for detecting foot-and-mouth disease antigen" (development product), respectively.

In an experiment for detecting an allergen protein of food, a saliva sample (G) was diluted by 10 times to prepare a diluted saliva sample, into the diluted saliva sample, each of an egg protein and a wheat protein, which were allergen proteins, was mixed so as to be around 25 ng/mL to obtain a sample, and the sample in a volume of 100 μL was subjected to immunochromatography.

On the other hand, in an experiment for detecting an enterohemorrhagic *Escherichia coli* O157, a saliva sample (G) was diluted by 10 times to prepare a diluted saliva sample, with the diluted saliva sample, "O157" (field strain, $1\times10^6$ cfu/mL) was diluted by 26 times to obtain a sample, and the sample in a volume of 100 μL was subjected to immunochromatography. In an experiment for detecting a foot-and-mouth disease virus, a saliva sample (R) having high inhibitory activity obtained in an examination different from that in Example (1-1) was used. The saliva sample (R) was diluted by 10 times to prepare a diluted saliva sample, into the diluted saliva sample, foot-and-mouth disease viruses (O/JPN/2010 strain) were mixed so as to be $10^{4.75}$ $TCID_{50}$/mL to obtain a sample, and the sample in a volume of 60 μL was subjected to immunochromatography.

Further, in each test, a control test in which PBS was added in place of the bovine saliva was provided, and the difference in the reactivity between the control test and the test in which bovine saliva was added was observed.

As a result, in particular, in the immunochromatography for detecting each of an egg protein, a wheat protein, and a foot-and-mouth disease, a decrease in the reactivity of close to almost 100% was observed by saliva. Further, in the immunochromatography for detecting "O157", a decrease in the reactivity of close to around 40% was observed. From these results, it was understood that the bovine saliva examined in Examples (1-1) showed the reaction inhibition against a wide range of antigens of IgG, bacteria, allergen proteins, viruses, and the like (Table 3).

TABLE 3

|  |  | Positive Test | |
|---|---|---|---|
|  |  | Test Line | Control Line |
| Immunochromatography for defecting an egg protein | PBS | 27.4 | 54.5 |
|  | Bovine Saliva | 0.0 | 0.0 |
| Immunochromatography for detecting a wheat protein | PBS | 15.6 | 189.1 |
|  | Bovine Saliva | 0.0 | 39.9 |
| Immunochromatography for detecting "O157" | PBS | 22.5 | 294.5 |
|  | Bovine Saliva | 13.0 | 75.3 |
| Immunochromatography for detecting a foot-and-mouth disease | PBS | 199.4 | 382.6 |
|  | Bovine Saliva | 0.0 | 43.3 |

(1-4) Influence by Dilution on Reaction Inhibition by Saliva Component

In a diagnostic kit or the like for humans, in order to avoid the reaction inhibition due to the contamination by saliva to a sample, there is an example in which dilution of a sample is recommended.

In this regard, by using a saliva sample being the same saliva sample used in Example (1-3), in order to examine whether or not the disappearance of the test line and the control line in immunochromatography for detecting *Campylobacter* (NH Immunochromato *Campylobacter*) was recovered by dilution, and in order to examine how many times of dilution were required for recovering the disappearance, the experiment was repeated multiple times while changing the dilution ratio.

As a result, the disappearance of both the test line and the control line was slightly recovered in the dilution of 5 times, however, the reaction did not recover completely even in the dilution of up to 50 times. As for the test line, only around 56% was recovered even in the dilution of 50 times (FIG. 2).

(Example 2) Screening of Agent for Suppressing Inhibition of Immune Reaction (2-1) Screening from Surfactant First, as a candidate for an agent for suppressing inhibition of immune reaction, various kinds of surfactants which had been conventionally considered to be effective for suppressing a substance causing immune reaction inhibition in a body fluid such as saliva were tested.

As the surfactant, by using various kinds of nonionic surfactants and amphoteric surfactants, in which a solubilization effect of mucin in saliva had been confirmed in Patent Document 1, a negative test and a positive test were performed.

In the negative test and the positive test, a saliva sample (G) was used in a similar manner as in Example (1-2) and the like, and NH Immunochromato *Campylobacter* and a *Campylobacter* dilute solution were used under conditions similar to those of Example (1-1).

As a result, a sufficient effect was not able to be confirmed with most of the surfactants (data not shown). The surfactants that were relatively effective were shown in the following (Table 4).

In a case of an anionic surfactant of sodium taurocholate hydrate (at a concentration of 2%), the control line was recovered, but the test line was not recovered. In a similar way, also in cases of deoxycholic acid sodium salt (at a concentration of 1 to 5%) and lauroyl sarcosine (at a concentration of 1 to 5%), each being an anionic surfactant, the control line was recovered, but the test line was not sufficiently recovered (Table 4). In a case of sodium dodecyl sulfate (SDS), the test line was slightly recovered, but from the consideration of the amount of *Campylobacter* bacterial cells added to the sample, it was determined that the line strength was not sufficient and the reaction was not recovered.

After all, a sufficient surfactant with which the test line was recovered together with the control line and no false positive reaction was shown was not able to be found.

TABLE 4

|  |  | Immunochromatography for detecting *Campylobacter* (MH Immunochromato *Campylobacter*) | |
|---|---|---|---|
|  |  | Test Line | Control Line |
| Without Surfactanct |  | 0.0 | 0.0 |
| Odium taurocholate hydrate | 0.1% | 12.3 | 11.1 |
|  | 0.5% | 8.2 | 38.0 |
|  | 1.0% | 9.5 | 50.9 |
|  | 2.0% | 8.7 | 191.7 |
|  | 5.0% | 6.9 | 326.8 |
| Sodium dodecyl sulfate (SDS) | 0.1% | 17.2 | 15.4 |
|  | 0.5% | 29.4 | 147.7 |
|  | 1.0% | 0.0 | 124.5 |
|  | 2.0% | 0.0 | 73.6 |
|  | 5.0% | 0.0 | 45.9 |
| Deoxycholic acid sodium salt | 0.1% | 10.0 | 22.2 |
|  | 0.5% | 0.0 | 33.8 |
|  | 1.0% | 0.0 | 146.3 |
|  | 2.0% | 0.0 | 199.7 |
|  | 5.0% | 0.0 | 214.6 |
| Lauroyl sarcosine | 0.1% | 10.4 | 26.9 |
|  | 0.5% | 17.5 | 139.2 |
|  | 1.0% | 0.0 | 150.0 |
|  | 2.0% | 0.0 | 161.7 |
|  | 5.0% | 0.0 | 165.5 |

(2-2) Screening from Column Resin

Next, screening was performed from various column resins such as cation exchange resins each having a sulfonic acid group or a carboxyl group, and the like, which had been used for pre-treatment of a pharyngeal-derived sample and had been effective for influenza virus detection in Patent Document 2.

The recovery rate in each of 26 types of columns in total of six types of strongly acidic cation exchange resins, two types of weakly acidic cation exchange resins, eight types of strongly basic anion exchange resins, four types of weakly basic anion exchange resins, and further two types of chelate resins, and four types of synthetic adsorbents was measured. At that time, the recovery rate was measured by taking the reactivity of a *Campylobacter* bacterial culture suspended in PBS as 100% as the positive control.

In detail, a sample in which 750 μL of *Campylobacter* killed bacteria was added into a saliva-diluted solution obtained by adding 21.24 mL of 1% BSA-containing borate buffer solution (pH 8.0) into 2.36 mL of bovine saliva was prepared, and 500 μL of the sample for testing was passed through a column packed with around 0.5 mL of each of the above-described resins.

Each of the obtained column-passed liquids was subjected to immunochromatography for detecting *Campylobacter* (NH Immunochromato *Campylobacter*, manufactured by NH Foods Ltd.), and the reactivity on each of the test line and the control line was measured (Table 5).

At that time, by taking the reactivity as 100% when a liquid obtained by suspending 750 μL of the above-described *Campylobacter* killed bacteria in 23.6 mL of PBS was subjected to NH Immunochromato *Campylobacter* as a positive control for inhibition removal, the recovery rate was calculated from the value of the test line when a liquid was passed through each of other columns.

TABLE 5

| | | | Test Line | Control Line | Recovery Rate of Test Line |
|---|---|---|---|---|---|
| Without Treatment | | | 8.9 | 31.5 | |
| Positive Control | | | 289.1 | 339.7 | 100% |
| Ion exchange resin | Strongly acidic cation exchange resin | 1 | 92.9 | 83.5 | 32% |
| | | 2 | 7.0 | 16.4 | 2% |
| | | 3 | 0.0 | 22.7 | 0% |
| | | 4 | 0.0 | 26.3 | 0% |
| | | 5 | 98.8 | 184.1 | 34% |
| | | 6 | 66.8 | 82.4 | 23% |
| | Weakly acidic cation exchange resin | 7 | 4.0 | 33.1 | 1% |
| | | 8 | 13.0 | 15.5 | 4% |
| | Strongly basic anion exchange resin | 9 | 11.0 | 11.8 | 4% |
| | | 10 | 13.3 | 11.4 | 5% |
| | | 11 | 13.9 | 15.3 | 5% |
| | | 12 | 9.6 | 22.7 | 3% |
| | | 13 | 83.6 | 158.5 | 29% |
| | | 14 | 16.4 | 17.9 | 6% |
| | | 15 | 6.4 | 41.2 | 2% |
| | | 16 | 11.5 | 24.1 | 4% |
| | Weakly basic anion exchange resin | 17 | 18.4 | 19.6 | 6% |
| | | 18 | 34.8 | 34.8 | 12% |
| | | 19 | 18.4 | 17.2 | 6% |
| | | 20 | 11.0 | 12.7 | 4% |
| Chelate resins | | 21 | 21.3 | 6.9 | 7% |
| | | 22 | 48.8 | 44.5 | 17% |
| Synthetic adsorbent | | 23 | 38.6 | 27.4 | 13% |
| | | 24 | 18.6 | 15.2 | 6% |
| | | 25 | 6.4 | 11.1 | 2% |
| | | 26 | 10.7 | 8.2 | 4% |

In the first results (Table 5) with these columns, among the strongly acidic cation exchange resins and the strongly basic anion exchange resins, multiple resins showing results of high recovery effect were found, however, when the test was conducted again, the reproducibility of the experiment was poor, and a stable effect was not obtained (data not shown).

After a column was packed with the ion exchange resin or the like, drying of the resin proceeded with the lapse of time in a stationary state, however, the progress was not constant due to various factors such as the way of packing of the column, and the indoor environment at that time. It was considered that such a variation in the dry state of the resin in the column caused unstable results.

(2-3) Stability of Strongly Acidic Cation Exchange Resin

In the following experiment, a strongly acidic cation exchange resin having a sulfonic acid group No. 5 (PK220, manufactured by Mitsubishi Chemical Corporation), which was most effective in the experiment of (2-2), was selected as a candidate for a temporary immune inhibition suppressing agent, and the stability was tested.

In a case of a strongly acidic cation exchange resin, if a column is left to stand after packing the column with a resin, the resin is dried with the lapse of time. There was a tendency that the results were not stable due to the variation in the dry state of the resin in the column. In view of this, a strongly acidic cation exchange resin PK220 (manufactured by Mitsubishi Chemical Corporation) was suspended in a 0.1% BSA-containing borate buffer solution, a conical column having an inner diameter of around 0.8 cm and a length of around 1.0 cm was packed with 0.3 g of the obtained suspension, the conical column was left to stand for one week while being either sealed or unsealed in a laboratory environment, and the stability was tested. Specifically, a saliva sample (R) was diluted by 10 times to prepare a diluted saliva sample, into the diluted saliva sample, foot-and-mouth disease viruses (O/JPN/2010 strain) were mixed so as to be $10^4$ $TCID_{50}$/mL to obtain a sample, and the sample in a volume of 60 µL was subjected to immunochromatography for detecting foot-and-mouth disease antigens. As a result, as shown in (Table 6), it was found that the reactivity to a foot-and-mouth disease virus in saliva was reduced due to the drying of the resin.

TABLE 6

| Storage condition (1 Week) | Appearance of resin | Reactivity to a foot-and-mouth disease virus in saliva (O/JPN/2010 $10^5 TCID_{50}$/1 mL of saliva) | |
|---|---|---|---|
| | | Visual Observation | IC Reader |
| Sealed | No change | + | 37.4 |
| Unsealed | Dried, decreased in volume | − | 0.0 |

(2-4) Effect of Suppressing Inhibition with Washing Solution of Strongly Acidic Cation Exchange Resin For the initial purpose of making the variation in the dry state of the resin uniform, 6 g of strongly acidic cation exchange resin PK220 (manufactured by Mitsubishi Chemical Corporation) was suspended in 18 mL of 0.1% BSA-containing borate buffer solution for immunochromatography, the obtained suspension was left to stand at 4° C. overnight, and the resin after the standing was used as a resin after washing to confirm the performance. Further, the supernatant after washing was collected. The reactivity of the control line of immunochromatography for detecting foot-and-mouth disease antigens to the saliva sample with the supernatant after washing was measured as a comparative example, together with the resin after washing.

As a result, surprisingly, the supernatant after washing showed almost 10 times stronger reactivity than that in the resin after washing (Table 7).

The reason why the supernatant after washing showed higher inhibition removal activity is presumed that the inhibition removal substance was soluble in a 0.1% BSA-containing borate buffer solution contained in the resin column, and from this, there is a high possibility that the high suppressive effect on immune inhibition by the strongly acidic cation exchange resin having a sulfonic acid group was due to the low-molecular compound having a sulfonic acid group that had been generated during the production process of the strongly acidic cation exchange resin and mixed as an impurity.

TABLE 7

| | Reactivity of the control line to saliva sample | |
|---|---|---|
| Treatment of resin | Visual Observation | IC Reader |
| Washing in developing solution (Supernatant) | + | 164.0 |
| Resin after washing in developing solution | ww+ | 17.9 |

(Example 3) Examination of Suppressive Effect on Immune Reaction Inhibition of Compound Having Sulfonic Acid Group (3-1) Recovery Effect of Reactive Inhibition by Saliva Sample For various sulfonic acid group-containing low-molecular compounds each having a straight-chain alkyl group, which are expected from the results of Example (2-4) to have a high suppressive effect on immune reaction inhibition, it was observed whether or not the inhibition to the reactivity of the control line by the bovine saliva sample in the immunochromatography for detecting foot-and-mouth disease antigens used in Example 1 (1-3) was recovered.

As a result, the compound that recovered the reaction inhibition of the control line at the lowest concentration was the straight-chain dodecylbenzenesulfonate. For this reason, it was presumed that the straight-chain dodecylbenzenesulfonate had the highest inhibition removal effect (Table 8).

Further, in various alkylsulfonic acid salts other than the straight-chain dodecyl benzenesulfonate, it was able to be confirmed that as the carbon number of the straight-chain alkyl group was larger, the effect was exerted at a lower concentration, and the effect was higher. In a case of the straight-chain sodium alkyl sulfonate, the control line was recovered with 5 or more carbon atoms. In a case of the straight-chain sodium alkylbenzene sulfonate, it was confirmed that the control line was recovered in a case where the straight-chain alkylbenzene sulfonic acid sodium had an alkyl group having 8 or 11 carbon atoms (Table 8).

TABLE 8

| | Addition concentration | Test Line | | Control Line | |
| --- | --- | --- | --- | --- | --- |
| | | Visual Observation | IC Reader | Visual Observation | IC Reader |
| Alkyl | | | | | |
| Sodium 1-undecanesulfonate (C11) | 0.50% | − | 0.0 | + | 175.9 |
| | 0.25% | − | 0.0 | + | 193.5 |
| | 0.13% | − | 0.0 | + | 130.7 |
| | 0.06% | − | 0.0 | + | 35.4 |
| | 0.03% | − | 0.0 | − | 0.0 |
| | 0.00% | − | 0 | − | 0.0 |
| Sodium 1-decanesulonate (C10) | 10.00% | N.T | | | |
| | 5.00% | − | 0.0 | + | 198.1 |
| | 2.50% | − | 0.0 | + | 99.9 |
| | 1.25% | − | 0.0 | + | 202.0 |
| | 0.63% | − | 0.0 | + | 104.9 |
| | 0.31% | − | 0.0 | + | 261.4 |
| | 0.16% | − | 0.0 | + | 84.4 |
| | 0.00% | − | 0.0 | − | 0.0 |
| Sodium 1-octanesulfonate (C8) | 10.00% | − | 0.0 | + | 173.7 |
| | 5.00% | − | 0.0 | + | 198.4 |
| | 2.50% | − | 0.0 | + | 302.1 |
| | 1.25% | − | 0.0 | + | 62.9 |
| | 0.63% | − | 0.0 | − | 0.0 |
| | 0.00% | − | 0.0 | − | 0.0 |
| Sodium 1-heptanesulfonate (C7) | 10.00% | − | 0.0 | + | 284.1 |
| | 5.00% | − | 0.0 | + | 275.1 |
| | 2.50% | − | 0.0 | + | 80.7 |
| | 1.25% | − | 0.0 | − | 0.0 |
| | 0.00% | − | 0.0 | − | 0.0 |
| Sodium 1-hexanesulfonate (C6) | 10.00% | − | 0.0 | + | 247.2 |
| | 5.00% | − | 0.0 | + | 27.7 |
| | 2.50% | − | 0.0 | − | 0.0 |
| | 1.25% | − | 0.0 | − | 7.9 |
| | 0.63% | − | 0.0 | − | 0.0 |
| | 0.00% | − | 0.0 | − | 0.0 |
| Sodium 1-pentanesulfonate (C5) | 10.00% | − | 0.0 | + | 117.2 |
| | 5.00% | − | 0.0 | − | 0.0 |
| | 2.50% | − | 0.0 | − | 0.0 |
| | 1.25% | − | 0.0 | − | 0.0 |
| | 0.63% | − | 0.0 | − | 0.0 |
| | 0.00% | − | 0.0 | − | 0.0 |
| Aromatic group | | | | | |
| Straight-chain sodium dodecylbenzenesulfonate (aromatic ring + C12) | 0.63% | − | 0.0 | + | 232.0 |
| | 0.31% | − | 0.0 | + | 205.6 |
| | 0.16% | − | 0.0 | + | 170.6 |
| | 0.08% | − | 0.0 | − | 73.6 |
| | 0.04% | − | 0.0 | − | 27.6 |
| | 0.00% | − | 0.0 | + | 0.0 |
| Sodium p-octylbenzenesulfonate (aromatic ring + C8) | 0.50% | − | 0.0 | + | 320.0 |
| | 0.13% | − | 0.0 | + | 298.5 |
| | 0.63% | − | 0.0 | + | 152.5 |
| | 0.03% | − | 0.0 | − | 0.0 |
| | 0.00% | − | 0.0 | − | 0.0 |

TABLE 8-continued

|  | Addition concentration | Test Line | | Control Line | |
| --- | --- | --- | --- | --- | --- |
|  |  | Visual Observation | IC Reader | Visual Observation | IC Reader |
| Sodium p-toluenesulfonate (aromatic ring + C1) | 2.00% | − | 0.0 | + | 309.3 |
|  | 1.00% | − | 0.0 | − | 70.7 |
|  | 0.50% | − | 0.0 | − | 0.0 |
|  | 0.25% | − | 0.0 | − | 0.0 |
|  | 0.00% | − | 0.0 | − | 0.0 |

(3-2) Examination of Most Suitable Addition Concentration

In view of this, into a developing solution for immunochromatography containing a straight-chain dodecylbenzenesulfonate, a saliva to which foot-and-mouth disease viruses (O/JPN/2010 strain) were added so as to be $10^6$ $TCID_{50}$/mL was added, and the obtained mixture was stirred. This stirred test solution was subjected to immunochromatography for detecting foot-and-mouth disease antigens.

When the examination was performed while changing the addition concentration of the straight-chain dodecylbenzenesulfonate, it has been understood that if the addition concentration of the straight-chain dodecylbenzenesulfonate is in the range of 0.05 to 1.0 (w/v) %, a foot-and-mouth disease virus in bovine saliva can be detected, and the range of 0.1 to 0.8 (w/v) % is preferred (Table 9).

TABLE 9

| Addition concentration of the straight-chain dodecylbenzenesulfonate | Visual Observation | Reader Measurement |
| --- | --- | --- |
| 0.625% | w+ | 21.2 |
|  | + | 57.3 |
| 0.3125% |  | 40.7 |
|  | + | 36.3 |
| 0.15625% | + | 35.4 |
|  | + | 57.2 |
| 0.078125% | ww+ | 14.5 |
|  | ± | 5.2 |
| 0% | − | 0 |

(Example 4) Effect of Suppressing Immune Reaction Inhibition by Aliphatic or Aromatic Alkylsulfonic Acid Salt (4-1) Detection Effect of Foot-and-Mouth Disease Virus-1

By using bovine saliva having strong inhibitory activity, a suppressive effect on inhibition due to the sodium sulfonate compound of the present invention was examined.

In detail, foot-and-mouth disease viruses (O/JPN/2010 strain) were added into 10 µL of bovine saliva sample so as to be $10^6$ $TCID_{50}$/mL, and then the obtained mixture was suspended so as to be a dilution of 10 times in a developing solution having an ordinary composition (containing Triton X-100), or a developing solution to which 0.3 (w/v) % of straight-chain sodium dodecylbenzenesulfonate or 2.5 w/v % of sodium octanesulfonate was added, and the obtained suspension was subjected to the immunochromatography for detecting foot-and-mouth disease antigens used in Example 1 (1-3).

As a result, in a case of only a developing solution, the foot-and-mouth disease virus was not able to be detected by visual observation because of the inhibition of saliva, and a reader measurement value of the test line showed 0.0, but in contrast, when the sodium sulfonate compound of the present invention was added into the saliva sample, the inhibitory action was suppressed, and the foot-and-mouth disease virus was able to be detected by a measurement value of a reader, and also by visual observation (Table 10).

In addition, further, it was also confirmed that no false positive results were obtained in a case of not containing the foot-and-mouth disease virus-containing saliva sample (Table 10).

At the same time, this result indicates that in Triton X-100 that is a nonionic surfactant in a developing solution, the suppressive effect can be hardly expected in a case where the inhibition of immune activity is strong.

TABLE 10

|  |  | Visual Observation | Reader Measurement |
| --- | --- | --- | --- |
| Saliva + foot-and-mouth disease virus | | | |
| Ordinary developing solution |  | − | 0.0 |
| Solution obtained by adding straight-chain sodium dodecylbenzenesulfonate | 0.3% | + | 125.3 |
|  |  | + | 143.4 |
| Solution obtained by adding sodium octanesulfonate | 2.5% | + | 52.9 |
|  |  | + | 20.6 |
| Only developing solution | | | |
| Solution obtained by adding straight-chain sodium dodecylbenzenesulfonate | 0.3% | − | 0.0 |
|  |  | − | 0.0 |
| Solution obtained by adding sodium octanesulfonate | 2.5% | − | 0.0 |
|  |  | − | 0.0 |

(4-2) Detection Effect of Foot-and-Mouth Disease Virus-2

In this experiment, the number of saliva samples similar to those in Example 1 (1-1) is increased, and into each of the saliva samples, a straight-chain sodium dodecylbenzenesulfonate is added, and the effect of suppressing immune inhibition of the straight-chain sodium dodecylbenzenesulfonate is confirmed.

Specifically, salivas collected from 49 bovines each being foot-and-mouth disease negative were purchased from Japan Bio Serum, each of the salivas was diluted with a 0.1% BSA containing borate buffer solution (pH 8.0) by 10 times to prepare a developing solution, and into the developing solution, 0.3 (w/v) % of straight-chain sodium dodecylbenzenesulfonate was added. Next, into the resultant mixture, foot-and-mouth disease viruses (O/JPN/2010 strain) were added so as to be $10^4$ $TCID_{50}$/mL, and the mixture was stirred. Each 140 µL of the obtained stirred mixture was added dropwise to immunochromatography for detecting foot-and-mouth disease antigens, and measurement was performed by visual observation and a reader (FIG. 3). Note that the sample numbers are not matched with those shown in (FIG. 1).

As a result, 47/49 samples were able to be correctly determined to be positive, and in view of the fact that only the 4/17 samples were able to be correctly determined to be positive in (Example 1-1), the effect of suppressing immune inhibition of the straight-chain sodium dodecylbenzenesulfonate was able to be confirmed.

(4-3) Improvement of False Positive Result by Alkyl Benzene Sulfonate

In the present Example, an effect of suppressing false positive results of the straight-chain sodium dodecylbenzenesulfonate is confirmed.

Specifically, among the bovine salivas collected in (4-2), the saliva showing a false positive result that was positive in immunochromatography for detecting foot-and-mouth disease antigens regardless of being foot-and-mouth disease negative was added into a 10-times diluted solution of an ordinary developing solution, and also added into a solution obtained by adding 0.3 (w/v) % of straight-chain sodium dodecylbenzenesulfonate into the 10-times diluted solution, and then both of the resultant solutions were subjected to the immunochromatography for detecting foot-and-mouth disease antigens in a similar manner as in Example 1 (1-3).

As a result, it was confirmed that by using a straight-chain sodium dodecylbenzenesulfonate, not only the reaction inhibition but also the false positive result was suppressed (Table 11).

TABLE 11

| Bovine Saliva | Test Line Visual Observation | Test Line IC Reader | Developing Solution |
| --- | --- | --- | --- |
| E-Day 4 | + | 23.0 | Ordinary developing solution |
|  | + | 15.4 |  |
| E-Day 5 | W+ | 8.3 |  |
|  | + | 21.9 |  |
| F-Day 1 | ± | 0.0 |  |
|  | + | 23.5 |  |
| E-Day 4 | − | 3.9 | Solution obtained by adding straight-chain sodium dodecylbenzenesulfonate |
|  | − | 0.0 |  |
| E-Day 5 | − | 0.0 |  |
|  | − | 0.0 |  |
| F-Day 1 | − | 0.0 |  |
|  | − | 0.0 |  |

(Example 5) Detection Effect of Allergen Protein Antigen

In the present Example, by using immunochromatography for detecting wheat proteins (FASTKIT Slim Wheat, manufactured by NH Foods Ltd.) with which almost 100% of the inhibitory activity was observed by the saliva sample in Example 1 (1-3), it was confirmed whether or not the reactivity was recovered by the straight-chain sodium dodecylbenzenesulfonate.

As a result, by using a straight-chain sodium dodecylbenzenesulfonate, the reactivity was recovered to a degree at which the detection can be obtained even by visual observation or an IC reader result (Table 12).

TABLE 12

FASTKIT Slim Wheat using a polyclonal antibody

|  | Visual Observation | Reader Measurement |
| --- | --- | --- |
| Saliva + Wheat protein (100 ng/mL) |  |  |
| Ordinally developing solution | − | 0.0 |
| Solution obtained by adding 0.25% straight-chain sodium dodecylbenzenesulfonate Wheat protein (100 ng/mL) | + | 33.2 |
| Ordinally developing solution | + | 43.1 |

(Example 6) Detection of Food Poisoning Bacteria O157

In the present Example, by using immunochromatography for detecting enterohemorrhagic *Escherichia coli* O157 (NH Immunochromato O157, manufactured by NH Foods Ltd.) with which almost 40% of the inhibitory activity was observed by the saliva sample in Example 1 (1-2), it is confirmed whether or not the reactivity is recovered by the straight-chain sodium dodecylbenzenesulfonate.

As a result, also with regard to the immunochromatography for detecting food poisoning bacteria O157, by using a straight-chain sodium dodecylbenzenesulfonate, the reaction was recovered, and the effect of suppressing reaction inhibition was able to be confirmed (Table 13).

TABLE 13

NH Immunochromato O157 using a polyclonal antibody

|  | Visual Observation | Reader Measurement |
| --- | --- | --- |
| Saliva + O157 $10^7$ CFU/mL |  |  |
| Ordinary developing solution | − | 0.0 |
| Solution obtained by adding 0.25% straight-chain sodium dodecylbenzenesulfonate O157 $10^7$ CFU/mL | + | 33.0 |
| Ordinary developing solution | + | 61.7 |

(Example 7) Screening of Quaternary Ammonium Salt

It has become apparent that the sodium sulfonate prevents the inhibition by saliva and the false positive results, and therefore, in the present Example, a quaternary ammonium salt that was focused because of being similar in the electric charge and the structure to a sulfonic acid sodium salt was examined whether or not there was any effect on the prevention of the inhibition by saliva or the false positive results.

Specifically, with respect to the quaternary ammonium salts shown in the following (1) to (14) of (Table 14), in a similar manner as in Example (3-1), by using bovine saliva having the highest inhibitory action selected in Example (1-1), each compound was added into a developing solution obtained by diluting the bovine saliva with a 1% BSA containing borate buffer solution (pH 8.0) by 10 times, and the obtained mixture was subjected to a negative test and a positive test by immunochromatography for detecting *Campylobacter* (NH Immunochromato *Campylobacter*).

TABLE 14

| No. | Name | Manufacturer | Code |
|---|---|---|---|
| ① | n-Ochyltrimethylammonium Bromide | Wako | 323-21122 |
| ② | Stearyltrimethylammonium Bromide | Wako | 324-92462 |
| ③ | Tetrabutylammonium Nitrate | Wako | 325-42741 |
| ④ | Tetrabutylammonium Hexafluorophosphate | Wako | 326-42732 |
| ⑤ | Lauryltrimethylammonium Chloride | Wako | 328-86992 |
| ⑥ | Tetrabuthlammonium Tribromide | Wako | 352-21232 |
| ⑦ | Methyltributylammonium Iodide | Wako | 354-27711 |
| ⑧ | Tetrabutylammoniumu Fluoride Trihydrate | Wako | 354-28992 |
| ⑨ | Tetramethylammonium Hydroxide Pentahydrate | Wako | 357-23622 |
| ⑩ | Benzyltributylammonium Chloride | Wako | 357-26802 |
| ⑪ | Tetrabutylammonium Dihydrogen Trifluoride | Wako | 358-19421 |
| ⑫ | Tetrabutylammonium Perchlorate | Wako | 358-20852 |
| ⑬ | Dodecyltrimethylammonium Bromide | Wako | 359-21122 |
| ⑭ | Methyotrioctylammonium Chloride | Wako | 359-24282 |

As a result, lauryl trimethylammonium chloride of (5), tetrabutylammonium fluoride of (8), tetrabutylammonium dihydrogen trifluoride of (11), dodecyl trimethylammonium bromide of (13), and methyl trioctylammonium chloride of (14), recovered both of the test line and the control line, and therefore, were taken as candidates for the immune inhibition suppressing agent of the present invention.

Next, the concentration condition of the methyl trioctylammonium chloride of (14) that had the highest recovery effect was examined.

As a result, it was found that in a case of methyl trioctylammonium chloride, *Campylobacter* was able to be detected when the concentration was 2.5 to 5.0 (w/v) % (data not shown).

(Example 8) Effect of Suppressing Immune Reaction Inhibition of Quaternary Ammonium Salt (8-1) Effect on Elimination of False Negative Result by Bovine and Swine Saliva Into bovine saliva BS-K16 with which the control line was inhibited and which was considered to cause a false negative result in Example (1-2), a *Campylobacter* bacterial culture was added so as to be $10^8$ CFU/mL (*Campylobacter*-added saliva).

The *Campylobacter*-added saliva was diluted 10 times with a solution obtained by dissolving a quaternary ammonium salt in PBS, and each of the obtained diluted solutions was subjected to NH Immunochromato *Campylobacter*.

In this regard, as the concentration at which each reagent was dissolved in PBS, the highest concentration within the range not impairing the reactivity to *Campylobacter* was selected.

As a result, a quaternary ammonium salt having a $C_{12}$-$C_{14}$ alky chain such as lauryl trimethylammonium chloride, dodecyl trimethylammonium bromide, or myristyl trimethylammonium bromide exhibited a high effect on the elimination of false negative results by saliva (Table 15).

TABLE 15

| Added test reagent concentraion | Saliva | Test Line Visual Observation | IC Reader | Control Line | |
|---|---|---|---|---|---|
| PBS (Control) | absence | + | 183.9 | 262.2 | |
| | BS-K16 | ± | 9.5 | 24.2 | ← False Negative |
| Lauryl trimethylammonium chloride 1% | BS-K16 | + | 144.7 | 124.4 | ← Reaction Recovered |
| Benzyl tributylammonium chloride 0.25% | BS-K16 | ± | 12.8 | 51.3 | ← False Negative (No effects) |
| Dodecyl trimethylammonium bromide 1% | BS-K16 | + | 119.7 | 112.6 | ← Reaction Recovered |
| Myristyl trimethylammonium bromide 1% | BS-K16 | W+ | 52.0 | 79.4 | ← Reaction Recovered |

(8-2) Effect on Elimination of False Positive Result by Bovine and Swine Saliva

Each of the bovine and swine saliva samples caused a false positive result in (8-1) was diluted 10 times with a solution obtained by dissolving a straight-chain dodecylbenzenesulfonic acid sodium salt in PBS, and also with a solution obtained by dissolving a straight-chain quaternary alkyl ammonium salt in PBS, and each of the obtained diluted solutions was subjected to NH Immunochromato *Campylobacter*.

As a result, it was confirmed that similarly to the case of the straight-chain sodium dodecylbenzenesulfonate, both of the lauryl trimethylammonium chloride and the dodecyl trimethylammonium bromide suppressed the false positive results derived from saliva (Table 16).

In view of the above, it has been understood that the quaternary ammonium salt can also be expected to have the suppressive effect on the immune inhibition that becomes a problem at the time of the measurement of various pathogen antigens, similar to the suppressive effect of the sulfonic acid compound having a straight-chain alkyl group.

TABLE 16

| Added test reagent, concentration | Saliva | Test Line Visual Observation | IC Reader | Control Line |
|---|---|---|---|---|
| PBS (Control) | BS-K10 | + | 43.7 | 178.5 |
| | SS-K44 | + | 150.8 | 264.7 |
| | SS-K53 | + | 114.7 | 303.2 |
| | SS-K61 | + | 210.2 | 205.8 |
| Straight-chain sodium dedecylbenzenesulfonate 0.3% | BS-K10 SS-K44 SS-K53 SS-K61 | ± | 7.6 | 252.6 |
| Lauryl trimethylammonium chloride 1% | BS-K10 SS-K44 SS-K53 SS-K61 | – – – | 0.8 3.4 0 | 180.7 161 153.4 |
| Dodecyl trimethylammonium bromide 1% | BS-K10 SS-K44 SS-K53 SS-K61 | – – – | 1.5 4.2 9.3 | 176.2 182.2 165.8 |

(Example 9) Effect of Suppressing Inhibition by Saliva in Immunochromatography for Detecting O157

(9-1) Effect on Elimination of False Negative Result by Bovine and Swine Saliva

First, a straight-chain dodecylbenzenesulfonic acid sodium salt, and multiple quaternary ammonium salts were each dissolved in PBS to obtain 1 (w/v) % solutions, and when each of the obtained solutions was subjected to NH Immunochromato O157, as shown in (Table 17), all of the compounds examined were negative, and therefore, were used in the following experiment.

TABLE 17

| Added test reagent, concentration | Test Line Visual Obsevation | IC Reader | Control Line |
|---|---|---|---|
| Straight-chain sodium dodecylbenzenesulfonate 1% | – | 2.4 | 507.6 |
| Lauryl trimethylammonium chloride 1% | – | 0.0 | 710.7 |
| Dodecyl trimethylammonium bromide 1% | – | 0.0 | 763.0 |
| Myristyl trimethylammonium bromide 1% | – | 3.0 | 750.6 |

As a result of the examination with the NH Immunochromato Campylobacter of Example (1-2), by using bovine saliva BS-K16 that was considered to cause a false negative result, a O157 bacterial culture was added into the bovine saliva BS-K16 so as to be 107 CFU/mL (O157-added saliva).

Next, the O157-added saliva was diluted 10 times with a solution obtained by dissolving a straight-chain dodecylbenzenesulfonic acid sodium salt in PBS, and also with a solution obtained by dissolving each of quaternary ammonium salts in PBS, and each of the obtained diluted solutions was subjected to NH Immunochromato O157.

As a result, it was confirmed that all of the straight-chain sodium dodecylbenzenesulfonate, the lauryl trimethylammonium chloride, the dodecyl trimethylammonium bromide, and the myristyl trimethylammonium bromide were effective for the elimination of false negative results derived from saliva (Table 18).

TABLE 18

| Added test reagent, concentration | Saliva | Test Line Visual Observation | IC Reader | Control Line | |
|---|---|---|---|---|---|
| PBS(Control) | absence | + | 162.6 | 741.6 | |
| | BS-K16 | W+ | 37.7 | 79.6 | ← Reaction Weakened |
| Straight-chain sodium dodecylbenzenesulfonate 1% | BS-K16 | + | 100.6 | 407.9 | ← Reaction Recovered |
| Lauryl trimethylammonium chloride 1% | BS-K16 | + | 121.3 | 413.6 | ← Reaction Recovered |
| Dodecyl trimethylammonium bromide 1% | BS-K16 | + | 153.6 | 468.2 | ← Reaction Recovered |
| Myristyl trimethylammonium bromide 1% | BS-K16 | + | 113.3 | 365.2 | ← Reaction Recovered |

(9-2) Effect on Elimination of False Positive Result by Bovine and Swine Saliva

As a result of the examination with the NH Immunochromato Campylobacter of Example (1-2), in a similar manner as in (9-1), the saliva (SS-K44) caused a false positive result was diluted 10 times with a solution obtained by dissolving a straight-chain dodecylbenzenesulfonic acid sodium salt in PBS, and also with a solution obtained by dissolving a quaternary ammonium salt in PBS, and each of the obtained diluted solutions was subjected to NH Immunochromato O157.

As a result, it was confirmed that all of the straight-chain sodium dodecylbenzenesulfonate, the lauryl trimethylammonium chloride, the dodecyl trimethylammonium bromide, and the myristyl trimethylammonium bromide were effective for the elimination of false positive results derived from saliva (Table 19).

TABLE 19

| Added test reagent, concentration | Saliva | Test Line Visual Observation | IC Reader | Control Line | |
|---|---|---|---|---|---|
| PBS (Control) | SS-K44 | + | 323.0 | 619.7 | ← False positive |
| Straight-chain sodium dodecylbenzenesulfonate 1% | SS-K44 | – | 4.0 | 701.2 | |
| Lauryl trimethylammonium chloride 1% | SS-K44 | – | 0.0 | 765.0 | |
| Dodecyl trimethylammonium bromide 1% | SS-K44 | ± | 6.3 | 779.3 | |

TABLE 19-continued

| Added test reagent, concentration | Saliva | Test Line Visual Observation | IC Reader | Control Line |
|---|---|---|---|---|
| Myristyl trimethylammonium bromide 1% | SS-K44 | ± | 10.9 | 746.8 |

(Example 10) Effect on Elimination of False Negative Result in Immunochromatography for Detecting Peanut Allergen (10-1) Effect on Elimination of False Negative Result by Bovine and Swine Saliva As a result of the examination with the NH Immunochromato *Campylobacter* of Example (1-2), a peanut protein was added into the bovine saliva BS-K16 that was considered to cause a false negative result so as to be 1 μg/mL, and a peanut protein-added saliva sample was prepared.

First, it was confirmed in advance that a solution obtained by dissolving a straight-chain dodecylbenzenesulfonic acid sodium salt in PBS, and also a solution obtained by dissolving a quaternary ammonium salt in PBS did not show false positive results at the test concentration (Table 20).

TABLE 20

| Added test reagent, concentration | Test Line Visual Observation | IC Reader | Control Line |
|---|---|---|---|
| Straight-chain sodium dodecylbenzenesulfonate 1% | − | 0.0 | 228.6 |
| Lauryl trimethylammonium chloride 1% | − | 1.5 | 194.8 |
| Dodecyl trimethylammonium bromide 1% | ± | 20.3 | 235.2 |
| Myristyl trimethylammonium bromide 1% | − | 6.3 | 197.9 |

Next, the peanut protein-added saliva sample was diluted 10 times with a solution obtained by dissolving a straight-chain dodecylbenzenesulfonic acid sodium salt in PBS, and also with a solution obtained by dissolving a quaternary ammonium salt in PBS, and each of the obtained diluted solutions was subjected to FASTKIT Slim Peanut.

As a result, it was confirmed that the straight-chain sodium dodecylbenzenesulfonate, the lauryl trimethylammonium chloride, and the myristyl trimethylammonium bromide, were able to recover the reactivity, and were effective for the elimination of false negative results derived from saliva (Table 21).

TABLE 21

| Added test reagent, concentration | Saliva | Test Line Visual Observation | IC Reader | Control Line | |
|---|---|---|---|---|---|
| PBS(Control) | absence | + | 152.8 | 313.7 | ← False |
|  | BS-K16 | − | 1.3 | 5.8 | Negative |
| Straight-chain sodium dodecylbenzenesulfonate 1% | BS-K16 | W+ | 17.1 | 186.6 | ← Reaction Recovered |
| Lauryl trimethylammonium chloride 1% | BS-K18 | W+ | 30.3 | 138.4 | ← Reaction Recovered |
| Myristyl trimethylammonium bromide 1% | BS-K16 | W+ | 22.8 | 102.9 | ← Reaction Recovered |

(Example 11) Effect on Elimination of False Negative Result in Immunochromatography for Detecting Various Allergens Since a quaternary ammonium salt was indicated to be effective for the elimination of false negative results by saliva in Example 10 or the like, it was confirmed whether or not these substances were effective for various allergen kits.

Specifically, various allergen proteins were each added into bovine saliva having strong inhibitory activity, and the resultant saliva was diluted 10 times with a developing solution to which a quaternary ammonium salt was added to prepare a sample solution, and the sample solution was subjected to immunochromatography for detecting various allergens. As the immunochromatography for detecting allergens, an egg, a wheat, a peanut, or crustaceans was used.

As a result, an effect of suppressing immune reaction inhibition was able to be confirmed in multiple quaternary ammonium salts (Table 22).

TABLE 22

|  | Egg | Wheat | Peanut | Crustaceans |
|---|---|---|---|---|
| Inhibition by saliva | presence | presence | presence | presence |
| Quaternary ammonium salt which were effective for the elimination of the inhibition by saliva, when added to the developing solution | Benzyl tributylammonium chloride | Lauryl trimethylammonium chloride, Dodecyl trimethylammonium bromide, Myristyl trimethylammonium bromide | Lauryl trimethylammonium chloride, Myristyl trimethylammonium bromide | Lauryl trimethylammonium chloride, Dodecyl trimethylammonium bromide, |

(Example 12) ELISA for Detecting *Campylobacter*

In the present Example, it is examined whether or not a false positive result by saliva is caused also in an ELISA, and further whether or not the false positive result is eliminated by the quaternary ammonium salt compound of the present invention in a similar manner as in the immunochromatography.

Specifically, an anti-*Campylobacter* monoclonal antibody (4B4: see JP 2009-77658 A) distributed by Osaka Prefectural Institute of Public Health was immobilized on a plate at a concentration of 5 μg/mL to prepare a solid phase plate.

Next, saliva diluted 10 time with the use of PBS or PBS containing various quaternary ammonium salt compounds so as to contain 107 CFU/mL of *Campylobacter* was added to the solid phase plate, and the resultant solid phase plate was incubated for one hour, and the washing was performed. Next, biotin-labeled 4B4 was added as a secondary antibody at a concentration of 1.6 μg/mL, and the incubation was performed for one hour, and the washing was performed.

Subsequently, streptavidin-horseradish peroxidase (HRP) was added, and the incubation was performed for 30 minutes, after the washing was performed, a HRP substrate was added, the incubation was performed for 20 minutes, a dilute sulfuric acid solution was added, and the reaction was terminated.

After that, absorbance in 450 nm was measured (at a reference wavelength of 620 nm).

As a result, as shown in (Table 23), even in the ELISA, it was confirmed that the immune reaction inhibition by saliva was recovered with the addition of a quaternary ammonium salt.

(Example 13) Verification of Effect of Suppressing Inhibition by Saliva with an ELISA Kit for Detecting Allergen It is examined whether or not a false negative result due to the inhibition by saliva is observed in an ELISA for detecting various allergens, and further, whether or not the false negative result is recovered by the straight-chain dodecylbenzenesulfonic acid sodium salt or the quaternary ammonium salt of the present invention in a similar manner as in the immunochromatography.

Specifically, as an ELISA kit for detecting peanut allergens, "FASTKIT ELISA Peanut (manufactured by NH Foods Ltd.)" was used, 5 μL of bovine saliva BS-K16 or PBS was added into 50 ng/mL or 25 ng/mL of peanut allergen protein, 50 μL of the obtained mixture was diluted with 45 μL of PBS solution of a straight-chain dodecylbenzenesulfonic acid sodium salt or a quaternary ammonium salt, and the obtained diluted solution was applied to the ELISA kit.

As a result, when saliva was added, a decrease in the reactivity was observed, and also in an ELISA, inhibition by saliva was confirmed. Further, it was confirmed that by adding lauryl trimethylammonium chloride, dodecyl trimethylammonium bromide, or myristyl trimethylammonium bromide of a quaternary ammonium salt into a reaction mixture, the reactivity was recovered (Table 24).

TABLE 23

| Campylobacter bacterial culture | Saliva | Added test reagent, concentraion | Well 1 | Well 2 | Ave. | |
|---|---|---|---|---|---|---|
| $10^7$ CFU/mL | absence | absence | 0.949 | 0.941 | 0.945 | |
| $10^7$ CFU/mL | BS-K16 | absence | 0.290 | 0.229 | 0.256 | ← Reactivity Decreased by Addition of Saliva |
| $10^7$ CFU/mL | BS-K16 | Lauryltrimethyl ammonium chloride 1% | 0.691 | 0.692 | 0.692 | Reactivity Recovered by Addition |
| $10^7$ CFU/mL | BS-K16 | Dodecyltrimethyl ammonium bromide 1% | 0.642 | 0.619 | 0.631 | Reactivity Recovered by Addition |
| $10^7$ CFU/mL | BS-K16 | Myristyltrimethyl ammonium bromide 1% | 0.605 | 0.582 | 0.594 | |
| $10^7$ CFU/mL | BS-K16 | Tetrabutyl ammonium fluoride trihydrate 1% | 0.369 | 0.365 | 0.367 | |
| $10^7$ CFU/mL | BS-K16 | Benzytributyl ammonium chloride 0.25% | 0.551 | 0.540 | 0.546 | Reactivity Recovered by Addition |
| absence | absence | absence | 0.005 | 0.004 | 0.005 | |

TABLE 24

| Added Antigen | Saliva | Added Compound | Well1 | Well2 | Ave. | |
|---|---|---|---|---|---|---|
| peanut protein 25 ng/mL | absence | absence | 0.786 | 0.794 | 0.79 | |
| peanut protein 12.5 ng/mL | absence | absence | 0.362 | 0.38 | 0.371 | |
| peanut protein 0 ng/mL | absence | absence | 0.004 | 0.003 | 0.0035 | |
| peanut protein 25 ng/mL | BS-K16 | PBS | 0.166 | 0.156 | 0.161 | ←Reactivity Decreased by Addition of Saliva |
| peanut protein 12.5 ng/mL | BS-K16 | PBS | 0.028 | 0.024 | 0.026 | |
| peanut protein 25 ng/mL | BS-K16 | (No.3) Tetrabutylammonium nitrate | 0.074 | 0.074 | 0.074 | |
| peanut protein 12.5 ng/mL | BS-K16 | (No.3) Tetrabutylammonium nitrate | 0.029 | 0.03 | 0.0295 | |
| peanut protein 25 ng/mL | BS-K16 | (No. 5) Lauryl trimethylammonium chloride | 0.527 | 0.538 | 0.5325 | Reaction Recovered |
| peanut protein 12.5 ng/mL | BS-K16 | (No.5) Lauryl trimethylammonium chloride | 0.294 | 0.29 | 0.292 | |
| peanut protein 25 ng/mL | BS-K16 | (No. 13) Dodecyl trimethylammonium bromide | 0.543 | 0.586 | 0.5545 | |
| peanut protein 12.5 ng/mL | BS-K16 | (No.13) Dodecyl trimethylammonium bromide | 0.298 | 0.296 | 0.296 | |
| peanut protein 25 ng/mL | BS-K16 | (No.30) Myristyl trimethylammonium bromide | 0.551 | 0.502 | 0.5265 | |
| peanut protein 12.5 ng/mL | BS-K16 | (No.30) Myristyl trimethylammonium bromide | 0.309 | 0.31 | 0.3095 | |
| absence | absence | (Straight-chain sodium dodecylbenzenesulfonate) | 0.003 | 0.003 | 0.003 | |
| absence | absence | (No.3) Tetrabutylammonium nitrate | 0.694 | 0.007 | 0.0055 | |
| absence | absence | (No.5) Lauryl trimethylammonium chloride | 0.004 | 0.004 | 0 004 | |
| absence | absence | (No.13) Dodecyl trimethylammonium bromide | 0.004 | 0.005 | 0.0045 | |
| absence | absence | (No.30) Myristyl trimethylammonium bromide | 0.004 | 0.004 | 0.004 | |

Other allergen proteins, specifically, wheat, sesame, and soybean allergen proteins were examined in a similar manner as in the case of peanut allergen by using "FASTKIT ELISA Wheat (manufactured by NH Foods Ltd.)", "FAST-KIT ELISA Sesame (manufactured by NH Foods Ltd.)", and "FASTKIT ELISA Soybean (manufactured by NH Foods Ltd.)", respectively, which are ELISA kits for detecting allergens.

As a result, it was able to be confirmed that also in other allergen proteins, multiple quaternary ammonium salts or a straight-chain dodecylbenzenesulfonic acid sodium salt was able to suppress the immune reaction inhibition by saliva, in a similar manner as in the case of peanut allergen protein (data not shown: Table 25).

TABLE 25

| | wheat | peanut | sesame | soybean |
|---|---|---|---|---|
| Inhibition by saliva | presence | presence | presence | presence |
| Compounds that were effective for the elimination of the inhibition by saliva, when added to the | Lauryl trimethylammonium chloride, Dodecyl trimethylammonium bromide, Myristyl trimethylammonium | Lauryl trimethylammonium chloride, Dodecyl trimethylammonium bromide, Myristyl trimethylammonium | Lauryl trimethylammonium chloride, Dodecyl trimethylammonium bromide, Myristyl trimethylammonium | Dodecyl trimethylammonium bromide, Myristyl trimethylammonium bromide, Straight-chairs sodium |

TABLE 25-continued

| | wheat | peanut | sesame | soybean |
|---|---|---|---|---|
| developing solution | bromide | bromide, Straight-chain sodium dodecylbenzenesulfonate | bromide | dodecylbenzenesulfonate |

The invention claimed is:

1. An immunoassay method for preventing inhibition of antigen-antibody binding interactions by a mucosal fluid, comprising,
 (a) preparing a test sample comprising a mucosal fluid from a subject,
 (b) bringing the test sample into contact with a target antigen-specific antibody,
 (c) adding an agent to suppress inhibition of antigen-antibody binding in the test sample, and
 (d) detecting the antigen-antibody binding in the test sample using antigen-antibody reaction
 wherein the agent comprises:
  a sulfonic acid compound of the formula $R^1$—$SO_3H$, or a salt thereof, or
  a quaternary ammonium ion of the formula $N^+$—$R^2R^3R^4R^5$ or a salt thereof,
 wherein $R^1$ is an unsubstituted straight-chain $C_5$-$C_{20}$ alkyl group, a straight-chain $C_1$-$C_{20}$ alkyl group substituted with a phenyl group having a straight-chain $C_5$-$C_{20}$ alkyl group, or a phenyl group substituted with a straight-chain $C_5$-$C_{20}$ alkyl group, and
 wherein $R^2$ to $R^5$ are each independently a straight-chain $C_1$-$C_{20}$ alkyl group unsubstituted or substituted with a phenyl group, and further
 wherein the agent is capable of suppressing false positive and/or false negative results of antigen-antibody binding caused by the mucosal fluid in the test sample.

2. The method according to claim 1,
 wherein in the formula of $R^1$—$SO_3H$, $R^1$ is an unsubstituted straight-chain $C_5$-$C_{20}$ alkyl group, or a phenyl group substituted with a straight-chain $C_5$-$C_{20}$ alkyl group.

3. The method according to claim 1,
 wherein in the formula of $N^+$—$R^2R^3R^4R^5$, $R^2$ to $R^5$ are each independently an unsubstituted straight-chain $C_1$-$C_{20}$ alkyl group, or
 $R^2$ to $R^4$ are each independently an unsubstituted straight-chain $C_1$-$C_{20}$ alkyl group and $R^5$ is a straight-chain $C_1$-$C_{20}$ alkyl group substituted with a phenyl group.

4. The method according to claim 1,
 wherein the salt of the ammonium ion is formed between the ammonium ion and a compound selected from the group consisting of hydrogen halide, nitric acid, hexafluorophosphoric acid, dihydrogen trifluoride, and perchloric acid.

5. The method according to claim 1,
 wherein the immunoassay is selected from the group consisting of an ELISA, an immunochromatography method, a Western blot method, an immunoblot method, an immunoprecipitation method, and a latex agglutination method.

6. The method according to claim 5,
 wherein the test sample comprises, as the mucosal fluid from the subject, at least one of saliva, sputum, a throat swab, a nasal swab, a nasal aspirate, and a keratoconjunctive swab.

7. The method according to claim 5,
 wherein the test sample comprises an antigen or antibody from a pathogen, a pathogenic microorganism, a hormone, or a prostaglandin.

8. The method according to claim 7,
 wherein the pathogen or the pathogenic microorganism is a pathogen or a pathogenic microorganism, selected from the group consisting of a foot-and-mouth disease virus, an influenza virus, an adenovirus, a respiratory syncytial virus, a coronavirus, a rabies virus, a *Bordetella pertussis*, a hemolytic *streptococcus*, a food poisoning bacterium, a *Chlamydia trachomatis*, and a *mycoplasma*.

9. A method for detecting a pathogen-specific antigen in a subject, comprising:
 (a) preparing a test sample comprising a mucosal fluid from a subject,
 (b) bringing the test sample into contact with a target antigen-specific antibody,
 (c) adding an agent to suppress inhibition of antigen-antibody binding in the test sample, and
 (d) detecting the antigen-antibody binding,
 wherein the agent comprises a sulfonic acid compound of the formula $R^1$—$SO_3H$ or a salt thereof, or a quaternary ammonium ion of the formula $N^+$—$R^2R^3R^4R^5$ or a salt thereof,
 wherein $R^1$ is an unsubstituted straight-chain $C_5$-$C_{20}$ alkyl group, a straight-chain $C_1$-$C_{20}$ alkyl group substituted with a phenyl group having a straight-chain $C_5$-$C_{20}$ alkyl group, or a phenyl group substituted with a straight-chain $C_5$-$C_{20}$ alkyl group, and
 wherein $R^2$ to $R^5$ are each independently a straight-chain $C_1$-$C_{20}$ alkyl group unsubstituted or substituted with a phenyl group, and
 wherein the agent is capable of suppressing false positive and/or false negative results of antigen-antibody binding caused by the mucosal fluid in the test sample.

10. The method according to claim 9,
 wherein the pathogenic disease is a disease caused by a pathogen or a pathogenic microorganism, selected from the group consisting of a foot-and-mouth disease virus, an influenza virus, an adenovirus, a respiratory syncytial virus, a coronavirus, a rabies virus, a *Bordetella pertussis*, a hemolytic *streptococcus*, a food poisoning bacterium, a *Chlamydia trachomatis*, and a *mycoplasma*.

11. The method according to claim 1, wherein the agent comprises a straight-chain dodecylbenzenesulfonate, lauryl trimethylammonium chloride, dodecyl trimethylammonium bromide, myristyl trimethylammonium bromide, or benzyl tributylammonium chloride.

12. The method according to claim 9, wherein the agent comprises a straight-chain dodecylbenzenesulfonate, lauryl trimethylammonium chloride, dodecyl trimethylammonium bromide, myristyl trimethylammonium bromide, or benzyl tributylammonium chloride.

13. The method according to claim 8, wherein the food poisoning bacterium comprises pathogenic *Campylobacter*, *Salmonella*, or *Escherichia coli*.

14. The method according to claim 10, wherein the food poisoning bacterium comprises pathogenic *Campylobacter*, *Salmonella*, or *Escherichia coli*.

* * * * *